(12) United States Patent
Batrakova et al.

(10) Patent No.: US 8,017,151 B2
(45) Date of Patent: Sep. 13, 2011

(54) AMPHIPHILIC POLYMER-PROTEIN CONJUGATES AND METHODS OF USE THEREOF

(75) Inventors: Elena V. Batrakova, Omaha (NE); Serguei V. Vinogradov, Omaha (NE); Alexander V. Kabanov, Omaha (NE)

(73) Assignee: Board of Regents of the University of Nebraska by and Behalf of the University of Nebraska Medical Center, Omaha, NE (US)

( * ) Notice: Subject to any disclaimer, the term of this patent is extended or adjusted under 35 U.S.C. 154(b) by 1964 days.

(21) Appl. No.: 10/935,293

(22) Filed: Sep. 7, 2004

(65) Prior Publication Data

US 2006/0051317 A1    Mar. 9, 2006

(51) Int. Cl.
    A61K 9/14      (2006.01)
    A61K 31/765    (2006.01)
    A61K 9/127     (2006.01)
    A61K 47/30     (2006.01)

(52) U.S. Cl. ............... 424/486; 424/78.37; 424/450; 514/772.3

(58) Field of Classification Search ........... 424/78.37, 424/486, 540; 514/772.3
See application file for complete search history.

(56) References Cited

U.S. PATENT DOCUMENTS

| | | | | |
|---|---|---|---|---|
| 5,427,778 | A | * | 6/1995 | Finkenaur et al. ......... 424/78.08 |
| 5,891,468 | A | * | 4/1999 | Martin et al. ............... 424/450 |
| 6,277,410 | B1 | | 8/2001 | Kabanov et al. |
| 6,277,828 | B1 | * | 8/2001 | Knepp et al. ................. 514/21 |
| 7,060,498 | B1 | * | 6/2006 | Wang ........................ 435/455 |
| 2002/0197256 | A1 | * | 12/2002 | Grewal ................... 424/144.1 |
| 2003/0108743 | A1 | * | 6/2003 | Anderson ............... 428/402.24 |

FOREIGN PATENT DOCUMENTS

WO     WO 00/09073     2/2000

OTHER PUBLICATIONS

Scherrmann ("Drug Delivery to brain via the blood-brain barrier," Vascular Pharmacology 38 (2002) 349-354).*
Ho et al. ("A Metal-Chelating PLURONIC for Immobilzation of Histidine-Tagged Proteins at Interfaces: Immobilization of Firefly Luciferase on Polystyrene Beads", in Langmuir 1998, 14, 3889-3894).*
Kirillova et al. ("The influence of pluronic and their conjugates with proteins on the rate of oxygen consumption by liver mitochondria and thymus lymphocytes," in Biotechnology and Applied Biochemistry (1993), 18, pp. 329-339, abstract enclosed). (Abstract).*
Yokoyama et al. (Characterization of physical entrapment and chemical conjugation of adriamycin in polymeric micelles and their design for in vivo delivery to a solid tumor, Journal of Controlled Release, vol. 50, Issues 1-3, Jan. 2, 1998, pp. 79-921).*

(Continued)

*Primary Examiner* — Blessing Fubara
(74) *Attorney, Agent, or Firm* — Patrick J. Hagan; Dann, Dorfman, Herrell and Skillman, P.C.

(57) ABSTRACT

Compositions and methods for transporting biologically active proteins and polypeptides, particularly across the blood-brain barrier, are provided.

21 Claims, 7 Drawing Sheets

OTHER PUBLICATIONS

Witt et al. ("Pluronic P85 Block Copolymer Enhances Opioid Peptide Analgesia," in Journal of Pharmacology and Experimental Therapeutics, Vo. 303, No. 2, 2002).*

Kabanov et al. ("Pluronic block copolymers as novel polymer therapeutic for drug and gene delivery," in Journal of Controlled Release, 82, 2002, pp. 189-212).*

Friden et al. "Blood Brain Barrier Penetration and in Vivo Activity of an NGF Conjugate," in Science, vol. 259, Jan. 15, 1993, pp. 373-377).*

Batrakova, et al., "Pluronic P85 Enhances the Delivery of Digoxin to the Brain: In Vitro and in Vivo Studies", J. of Pharmacology and Experimental Therapeutics, 296: 551-557 (2001).

Batrakova, et al., "Mechanism of Pluronic Effect on P-Glycoprotein Efflux System in Blood-Brain Barrier: Contributions of Energy Depletion and Membrane Fluidization", J. of Pharmacology and Experimental Therapeutics, 299: 483-493 (2001).

Batrakova, et al., "Optimal Structure Requirements for Pluronic Block Copolymers in Modifying P-glycoprotein Drug Efflux Transporter Activity in Bovine Brain Microvessel Endothelial Cells", J. of Pharmacology and Experimental Therapeutics, 304: 845-854 (2003).

Caliceti, et al., "Pharmacokinetic and biodistribution properties of poly(ethylene glycol)-protein conjugates", Adv. Drug Deliv. Rev., 55(10):1261-77 (2003).

* cited by examiner

AMPHIPHILIC POLYMER-PROTEIN CONJUGATES AND METHODS OF USE THEREOF

FIELD OF THE INVENTION

The present invention relates to the transport of biologically active proteins across biological membranes, particularly across the blood-brain barrier.

BACKGROUND OF THE INVENTION

The blood-brain barrier (BBB) is one of the most restrictive barriers in biology. Numerous factors work together to create this restrictive barrier. Electron microscopy studies have demonstrated that tight junctions between brain vascular endothelial cells and other endothelial cell modifications (e.g., decreased pinocytosis, lack of intracellular fenestrate) prevented the formation of a plasma ultrafiltrate. Enzymatic activity at the BBB further limits entry of some substances, especially of monoamines and some small peptides (Baranczyk-Kuzma and Audus (1987) J. Cereb. Blood Flow Metab., 7:801-805; Hardebo and Owman (1990) Pathophysiology of the Blood-Brain Barrier, pp. 41-55 (Johansson et al., Eds.) Elsevier, Amsterdam; Miller et al. (1994) J. Cell. Physiol., 161:333-341; Brownson et al. (1994) J. Pharmacol. Exp. Ther., 270:675-680; Brownlees and Williams (1993) J. Neurochem., 60:793-803). Saturable, brain-to-blood efflux systems, such as p-glycoprotein (Pgp), also prevent the accumulation of small molecules and lipid soluble substances (Taylor, E. M. (2002) Clin. Pharmacokinet., 41:81-92; Schinkel et al. (1996) J. Clin. Invest., 97:2517-2524). Peripheral factors such as protein binding/soluble receptors, enzymatic degradation, clearance, and sequestration by tissues also affect the ability of a substance to cross the BBB by limiting presentation; these factors are especially important for exogenously administered substances (Banks and Kastin (1993) Proceedings of the International Symposium on Blood Binding and Drug Transfer, pp. 223-242 (Tillement et al., Eds.) Fort and Clair, Paris).

Substances are able to cross the BBB by way of a few pathways. Such pathways include: 1) saturable transporter systems, 2) adsorptive transcytosis wherein the compound to be transported is internalized by a cell in the BBB and routed to the abluminal surface for deposition into the brain intracellular fluid compartment, 3) transmembrane diffusion wherein the substance dissolves into the lipid bilayer which forms the membranes of the cells comprising the BBB, and 4) extracellular pathways wherein compounds exploit the residual leakiness of the BBB.

The hydrophilicity, the lack of stability due to enzymatic or chemical degradation, and the lack of transport carriers capable of shuttling polypeptides across cell membranes all play a part in precluding most polypeptides from transport into the brain. Several approaches to modify polypeptides to alter their BBB permeability have been attempted including: 1) conjugation with proteins that naturally cross the BBB (Raub and Audus (1990) J. Cell. Sci., 97:127-138; Banks and Broadwell (1994) J. Neurochem., 62:2404-2419; Bickel et al. (2001) Adv. Drug Deliv. Rev., 46:247-279); 2) modifying the polypeptide with cationic groups, i.e. "cationization" (Kumagai et al. (1987) J. Biol. Chem., 262:15214-15219; Triguero et al. (1989) Proc. Natl. Acad. Sci., 86:4761-4765; Triguero et al. (1991) J. Pharmacol. Exp. Ther., 258:186-192; Bickel et al. (2001) Adv. Drug Deliv. Rev., 46:247-279); 3) modifying the polypeptides with polyethylene glycol (PEG; Delgado et al. (1992) Crit. Rev. Ther. Drug. Carrier. Syst., 9:249-304; 4) linking the polypeptides to antibodies targeting certain cellular receptors (Zhang and Pardridge (2001) Brain Res., 889: 49-56; Zhang and Pardridge (2001) Stroke, 32:1378-1384; Song et al. (2002) J. Pharmacol. Exp. Ther., 301:605-610) and 5) stearoylation of the polypeptide (Chekhonin et al. (1991) FEBS Lett., 287:149-152; Chopineau et al. (1998) J. Contr. Release, 56:231-237; Chekhonin et al. (1995) Neuroreport., 7:129-132).

Another method employed to increase BBB transport is by the use of Pluronic® block copolymers (BASF Corporation, Mount Olive, N.J.). Pluronic® block copolymers (listed in the US and British Pharmacopoeia under the name "poloxamers") consist of ethylene oxide (EO) and propylene oxide (PO) segments arranged in a basic A-B-A structure: $EO_a$—$PO_b$-$EO_a$. This arrangement results in an amphiphilic copolymer, in which altering the number of EO units (a) and the number of PO units (b) can vary its size, hydrophilicity, and lipophilicity. A characteristic of Pluronic® copolymers is the ability to self-assemble into micelles in aqueous solutions. The noncovalent incorporation of drugs into the hydrophobic PO core of the Pluronic® micelle imparts to the drug increased solubility, increased metabolic stability, and increased circulation time (Kabanov and Alakhov (2002) Crit. Rev. Ther. Drug Carrier Syst., 19:1-72; Allen et al. (1999) Coll. Surfaces, B: Biointerfaces, 16:3-27).

Pluronic® micelles conjugated with antibody to alpha 2GP have been shown to deliver neuroleptic drugs and fluorescent dyes to the brain in mice (Kabanov et al. (1989) FEBS Lett., 258:343-345; Kabanov et al. (1992) J. Contr. Release, 22:141-157). Additionally, selected Pluronic® block copolymers, such as P85, are potent inhibitors of p-glycoprotein (Pgp) and increase entry of the Pgp-substrates to the brain across BBB (Batrakova et al. (1998) Pharm. Res., 15:1525-1532; Batrakova et al. (1999) Pharm. Res., 16:1366-1372; Batrakova et al. (2001) J. Pharmacol. Exp. Ther., 296:551-557). The mechanism of the Pluronic® effect in the latter case involves decreases in membrane microviscosity by Pluronic® and depletion of intracellular ATP, which together blocked the Pgp efflux function in brain endothelial cells (Batrakova et al. (2001) J. Pharmacol. Exp. Ther., 299:483-493; Batrakova et al. (2003) J. Pharmacol. Exp. Ther., 304: 845-854). Pluronic® did not induce toxic effects in the BBB as revealed by the lack of alteration in paracellular permeability of the barrier (Batrakova et al. (1998) Pharm. Res., 15:1525-1532; Batrakova et al. (2001) J. Pharmacol. Exp. Ther., 296:551-557). It has been noted that Pluronic® fluorescently labeled with FITC can accumulate in the brain following systemic administration in mice (Kabanov et al. (1992) J. Contr. Release, 22:141-157). Furthermore, selected Pluronic® copolymers can cross the membranes of the brain endothelial cells (Batrakova et al. (2003) J. Pharmacol. Exp. Ther., 304:845-854).

Notably, Pluronic® copolymers have also been used in combination with anticancer drugs in the treatment of multidrug resistant (MDR) cancers (Alakhov et al. (1996) Bioconjug. Chem., 7:209-216; Alakhov et al. (1999) Colloids Surf., B: Biointerfaces, 16:113-134; Venne et al. (1996) Cancer Res., 56:3626-3629). Indeed, Phase I and II clinical trial are being performed on doxorubicin formulated with Pluronic® ("SP1049C") for the treatment of adenocarinoma of esophagus and soft tissue sarcoma, both cancers with high incidence of MDR (Ranson et al. (2002) 5th international symposium on polymer therapeutics: from laboratory to clinical practice, pp. 15, The Welsh School of Pharmacy, Cardiff University, Cardiff, UK).

SUMMARY OF THE INVENTION

The present invention broadly relates to compositions and methods for the delivery of biologically active proteins across biological membranes, specifically, the blood brain barrier, wherein the protein is conjugated with an amphiphilic polymer.

According to one aspect of the invention, a method for delivering a protein across the blood-brain barrier into the central nervous system of an animal is provided. The method comprises administering to the animal a conjugate comprising the protein conjugated to an amphiphilic block copolymer by a cleavable linker moiety. In a preferred embodiment, the linker is cleaved or substantially cleaved either while traversing the BBB or once having crossed the BBB.

In a particular embodiment of the invention, the amphiphilic block copolymer is a copolymer comprising at least one poly(oxyethylene) segment and at least one poly(oxypropylene) segment. In yet another embodiment, the amphiphilic block copolymer is of the formula selected from the group consisting of Formulas I-VI, as shown below. In still another embodiment, the amphiphilic block copolymer is a Pluronic®, such as Pluronic® L121.

According to another aspect of the invention, the amphiphilic block copolymer of the instant invention has a hydrophilic-lipophilic balance (HLB) of less than or equal to 20, preferably less than or equal to 16, more preferably less than or equal to 12, and most preferably less than or equal to 8.

According to yet another aspect of the invention, the amphiphilic block copolymer of the instant invention has a hydrophobe molecular weight greater than or equal to 1500 Da, preferably greater than or equal to 2000 Da, more preferably greater than or equal to 2500 Da, and most preferably greater than or equal to 3000 Da.

In accordance with another aspect of the present invention, the cleavable linker moiety linker of the conjugate of the instant invention comprises a disulfide bond. Alternatively, the cleavable linker moiety linker comprises a recognition site for a protease. Exemplary proteases include, without limitation, endosomal cathepsins, cathepsin B, lysosomal proteases, and colagenase.

According to another aspect of the invention, the protein of the conjugates of the instant invention is a therapeutic protein. Exemplary therapeutic proteins include, without limitation, cytokines; growth factors such as, without limitation, epidermal growth factor (EGF), basic fibroblast growth factor (bFGF), and nerve growth factor (NGF); amyloid beta binders; enkephalin; modulators of α-, β-, and/or γ-secretases; Glial-derived neutrotrophic factor (GDNF); vasoactive intestinal peptide; acid alpha-glucosidase (GAA); acid sphingomyelinase; iduronate-2-sultatase (I2S); α-L-iduronidase (IDU); β-Hexosaminidase A (HexA); Acid β-glucocerebrosidase; N-acetylgalactosamine-4-sulfatase; and α-galactosidase A.

BRIEF DESCRIPTIONS OF THE DRAWING

FIG. 1 is a scheme for the synthesis of Pluronic®-HRP conjugates. Pluronic®-Amine is activated by bifunctional reagents (DSP or DSS) to obtain hydroxysuccinimide derivatives of Pluronic® (A and B, respectively) capable of reacting with the protein aminogroups (Step 1). The excess of the reagents was removed by gel filtration, and the activated polymers were immediately reacted with HRP (Step 2).

FIGS. 2A and 2B are graphs of the chromatographic isolation of HRP-Pluronic® conjugates. The peaks correspond to (1) bis-substituted HRP; (2) mono-substituted HRP; and (3) unmodified HRP. The substitution degree in each fraction was confirmed by the TNBS assay.

FIG. 3 is a scheme showing alternative methods for synthesis of Pluronic®-HRP conjugates with degradable links. In Method 1, N-hydroxybenzotriazolyde derivative of Pluronic® is prepared by reacting with bis-(N-hydroxybenzotriazolyl) phenylphosphate and then used for modification of HRP. In Method 2, Pluronic®-succinate is obtained by reacting the polymer with succinic anhydride and then activated by water-soluble ethyl dimethylaminopropyl carbodiimide (EDC) to modify HRP.

Figure 7A:
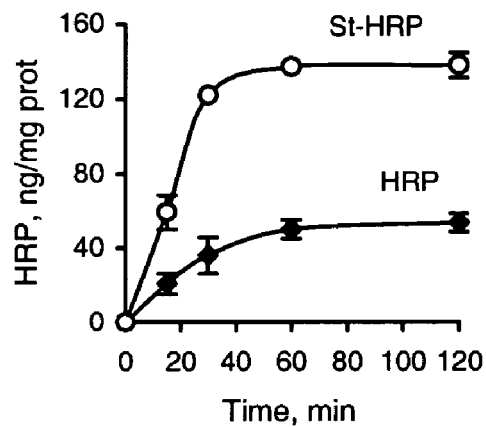
Figure 7B:
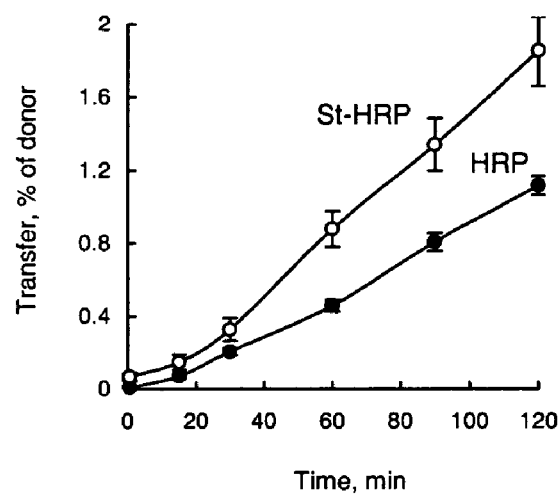

FIG. 7A is a graph depicting the binding of unmodified HRP and stearoylated (St-HRP) with BBMEC monolayers as a function of time. Data are mean±SEM (n=4). (*) shows significant difference between HRP and St-HRP groups. FIG. 7B is a graph depicting the apical to basolateral permeability of HRP and St-HRP in BBMEC monolayers as a function of time. Data are mean±SEM (n=4). (*) shows significant difference between HRP and St-HRP groups.

DETAILED DESCRIPTION OF THE INVENTION

In accordance with the present invention, compositions and methods are provided for the transport of biologically active proteins across biological membranes, particularly across the blood-brain barrier. Specifically, the proteins are conjugated to amphiphilic polymers for transport across the BBB. The conjugation of amphiphilic polymers to the proteins preferably results in i) increased stability of the protein in circulation by means of the formation of a protective hydrophilic polymer layer around the protein and ii) increasing the interaction of the protein with the BBB due to the influence of the lipophilic portions of the amphiphilic polymer.

In a preferred embodiment of the instant invention, the protein is conjugated to the amphiphilic polymer via a degradable linker. Preferably, the linker is cleaved or substantially cleaved during transport through the BBB and/or after crossing the BBB. Such cleavable linkers allow for the release of free protein in the central nervous system (CNS).

In a particular embodiment of the invention, the amphiphilic polymers are conjugated to the protein via modification of a free amino, thiol, or carboxyl group on the protein. The amphiphilic polymer may be mono-activated through a linker.

In yet another embodiment of the invention, methods are provided for the administration of amphiphilic polymer-protein conjugates comprising a therapeutic protein to a patient in order to treat conditions in which the therapeutic protein is known to be effective. In a particular embodiment, the conjugates are administered systemically. According to another aspect, the conjugates are administered in combination with free amphiphilic polymer.

In accordance with another embodiment of the invention, fatty acids are conjugated to the protein of interest and the resultant conjugates are employed in the methods described hereinabove for the amphiphilic polymer-conjugates. In a preferred embodiment, the fatty acids are essential fatty acids such as, without limitation, linoleic acid and alpha-linoleic acid.

I. Definitions

The following definitions are provided to facilitate an understanding of the present invention:

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

As used herein, the term "lipophilic" refers to the ability to dissolve in lipids.

As used herein, the term "hydrophilic" means the ability to dissolve in water.

As used herein, the term "amphiphilic" means the ability to dissolve in both water and lipids. Typically, an amphiphilic compound comprises a hydrophilic portion and a lipophilic portion.

The term "substantially cleaved" refers to the cleavage of the amphiphilic polymer from the protein of the conjugates of the instant invention, preferably at the linker moiety. "Substantial cleavage" occurs when at least 50% of the conjugates are cleaved, preferably at least 75% of the conjugates are cleaved, more preferably at least 90% of the conjugates are cleaved, and most preferably at least 95% of the conjugates are cleaved.

II. Amphiphilic Polymers

Amphiphilic polymers according to the instant invention are preferably amphiphilic block copolymers. Generally, amphiphilic block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block.

Amphiphilic block copolymers which may be used in the practice of this invention are exemplified by the block copolymers having the formulas:

A-B-A type:

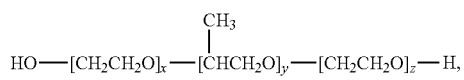
(I)

A-B type:

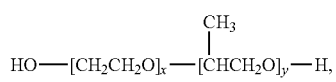
(II)

B-A-B type:

(III)

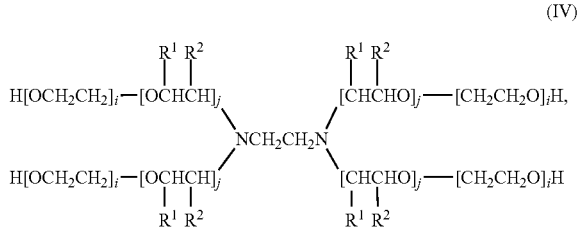
(IV)

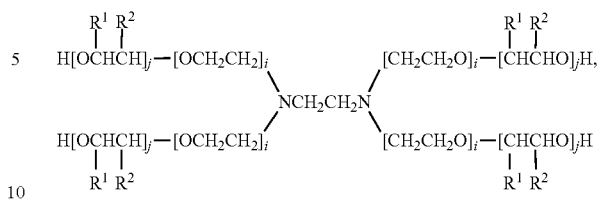
(V)

in which x, y, z, i, and j have values from about 2 to about 800, preferably from about 5 to about 200, more preferably from about 5 to about 80, and wherein for each $R^1$, $R^2$ pair, as shown in formula (IV) and (V), one is hydrogen and the other is a methyl group. Formulas (I) through (III) are oversimplified in that, in practice, the orientation of the isopropylene radicals within the B block will be random. This random orientation is indicated in formulas (IV) and (V), which are more complete. Such poly(oxyethylene)-poly(oxypropylene) compounds have been described by Santon (Am. Perfumer Cosmet. (1958) 72(4):54-58); Schmolka (Loc. cit. (1967) 82(7):25-30), Schick, ed. (Non-ionic Suifactants, Dekker, N.Y., 1967 pp. 300-371). A number of such compounds are commercially available under such generic trade names as "lipoloxamers", "Pluronics®," "poloxamers," and "synperonics." Pluronic® copolymers within the B-A-B formula, as opposed to the A-B-A formula typical of Pluronics®, are often referred to as "reversed" Pluronics®, "Pluronic® R" or "meroxapol."

The "polyoxamine" polymer of formula (IV) is available from BASF under the tradename Tetronic®. The order of the polyoxyethylene and polyoxypropylene blocks represented in formula (IV) can be reversed, creating Tetronic R®, also available from BASF (see, Schmolka, J. Am. Oil. Soc. (1979) 59:110).

Polyoxypropylene-polyoxyethylene block copolymers can also be designed with hydrophilic blocks comprising a random mix of ethylene oxide and propylene oxide repeating units. To maintain the hydrophilic character of the block, ethylene oxide would predominate. Similarly, the hydrophobic block can be a mixture of ethylene oxide and propylene oxide repeating units. Such block copolymers are available from BASF under the tradename Pluradot™.

The hydrophobic/hydrophilic properties of a given block copolymer depend upon the ratio of the number of oxypropylene groups to the number of oxyethylene groups. For a composition comprising an A-B-A type block copolymer of poly(oxyethylene)-poly(oxypropylene), for example, this relationship, taking into account the molecular masses of the central hydrophobic block and the terminal hydrophilic blocks, can be expressed as follows:

$$n=(H/L)(1.32)$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n (which is related to the hydrophilic-lipophilic balance (HLB) described hereinbelow) as defined as:

$$n=(|B|/|A|) \times (b/a)$$

where |B| and |A| are the number of repeating units in the hydrophobic and hydrophilic blocks of the copolymer, respectively, and b and a are the molecular weights for the respective repeating units.

Selecting a block copolymer with the appropriate n value depends upon the hydrophobic/hydrophilic properties of the specific agent, or the composite hydrophilic/hydrophilic properties of a mixture of agents to be formulated. One aspect of the present invention involves utilizing a mixture of different block-copolymers of poly(oxyethylene)-poly(oxypropylene) to achieve a prescribed hydrophobic-hydrophilic balance. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N=(1.32)[(H_1 m_1)/((L_1)(m_1+m_2))+(H_2 m_2)/((L_2)(m_1+m_2))]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion of the first block-copolymer; and $m_2$ is the weight proportion of the second block copolymer.

An even more general case of a mixture of K block copolymers containing hydrophobic B-type block copolymers and hydrophilic A-type block copolymers, the N value can be expressed as follows:

$$N = (b/a)\sum_{i=1}^{k}[(|B|_i/|A|_i),(m_i/M)]$$

where $|A|_i$ and $|B|_i$ are the numbers of repeating units in the hydrophilic (A-type) and hydrophobic (B-type) blocks, respectively, of the i-th block copolymer, m is the weight proportion of this block copolymers, M is the sum of weight proportions of all block copolymers in the mixture $$M = \sum_{i=1}^{k} m_i$$

and a and b are the molecular weights for the repeating units of the hydrophilic and hydrophobic blocks of these block copolymers, respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene) (EO-PO). Where mixtures of block copolymers are used, a value N will be used, which value will be the weighted average of n for each contributing copolymer, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of serum proteins.

A number of Pluronic® copolymers are designed to meet the following formula:

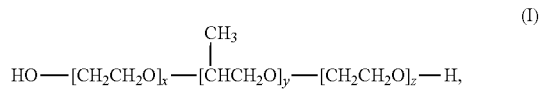

$$HO-[CH_2CH_2O]_x-[CHCH_2O]_y-[CH_2CH_2O]_z-H, \quad (I)$$

with CH$_3$ branch on the middle block.

The ordinarily skilled artisan will recognize that the values of x, y, and z will usually represent a statistical average and that the values of x and z are often, though not necessarily, the same. The characteristics of a number of Pluronic® copolymers corresponding to formula (I) are as follows:

TABLE 1

| Copolymer | Hydrophobe Weight | CMC (% w/v) | Hydrophobe percentage |
|---|---|---|---|
| Pluronic ® L61 | 1750 | 0.0003 | 90 |
| Pluronic ® L64 | 1750 | 0.002 | 60 |
| Pluronic ® F68 | 1750 | 4-5 | 20 |
| Pluronic ® P85 | 2250 | 0.005-0.007 | 50 |
| Pluronic ® F127 | 4000 | 0.003-0.005 | 30 |
| Pluronic ® F108 | 3250 | 0.0035-0.007 | 20 |

These critical micelle concentrations (CMC) values were determined by the surface tension method described in Kabanov et al. (Macromolecules (1995) 28: 2303-2314).

These block copolymers can be prepared by the methods set out, for example, in U.S. Pat. No. 2,674,619 and are commercially available from BASF under the trademark Pluronic®. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits designate the molecular mass of the central PO block. To decipher the code, one should multiply the corresponding number by 300 to obtain the approximate molecular mass in daltons (Da). Therefore Pluronic nomenclature provides a convenient approach to estimate the characteristics of the block copolymer in the absence of reference literature. For example, the code 'F127' defines the block copolymer, which is in solid flake form, has a PO block of 3600 Da (12×300) and 70% weight of EO. The precise molecular characteristics of each Pluronic® block copolymer can be obtained from the manufacturer.

Additional specific poly(oxyethylene)-poly(oxypropylene) block copolymers which can be used in practicing this invention include Pluronic® and Pluronic®-R block copolymers, such as those listed in Table 2.

TABLE 2

| Pluronic ® | Hydrophobe Weight | Hydrophobe % | Pluronic-R ® | Hydrophobe Weight | Hydrophobe % |
|---|---|---|---|---|---|
| L31 | 950 | 90 | 10R5 | 1000 | 50 |
| L35 | 950 | 50 | 10R8 | 1000 | 20 |
| F38 | 900 | 20 | 12R3 | 1200 | 70 |
| L42 | 1200 | 80 | 17R1 | 1700 | 90 |
| L43 | 1200 | 70 | 17R2 | 1700 | 80 |
| L44 | 1200 | 60 | 17R4 | 1700 | 60 |
| L61 | 1750 | 90 | 17R8 | 1700 | 20 |

TABLE 2-continued

| Pluronic ® | Hydrophobe Weight | Hydrophobe % | Pluronic-R ® | Hydrophobe Weight | Hydrophobe % |
|---|---|---|---|---|---|
| L62 | 1750 | 80 | 22R4 | 2200 | 60 |
| L63 | 1750 | 70 | 25R1 | 2500 | 90 |
| L64 | 1750 | 60 | 25R2 | 2500 | 80 |
| P65 | 1750 | 50 | 25R4 | 2500 | 60 |
| F68 | 1750 | 20 | 25R5 | 2500 | 50 |
| L72 | 2050 | 80 | 25R8 | 2500 | 50 |
| P75 | 2050 | 50 | 31R1 | 3100 | 90 |
| F77 | 2050 | 30 | 31R2 | 3100 | 80 |
| L81 | 2250 | 90 | 31R4 | 3100 | 60 |
| P84 | 2250 | 60 | | | |
| P85 | 2250 | 50 | | | |
| F87 | 2250 | 30 | | | |
| F88 | 2250 | 20 | | | |
| L92 | 2750 | 80 | | | |
| F98 | 2750 | 20 | | | |
| L101 | 3250 | 90 | | | |
| P103 | 3250 | 70 | | | |
| P104 | 3250 | 60 | | | |
| P105 | 3250 | 50 | | | |
| F108 | 3250 | 20 | | | |
| L121 | 4000 | 90 | | | |
| L122 | 4000 | 80 | | | |
| L123 | 4000 | 70 | | | |
| F127 | 4000 | 30 | | | |

Other specific poly(oxyethylene)-poly(oxypropylene) block polymers which can be included in compositions described herein are the Tetronic® and Tetronic® R nonionic surfactants of formula (IV) and (V), above, which are tetrafunctional block copolymers derived from the addition of ethylene oxide and propylene oxide to ethylenediamine. Tetronic® and Tetronic® R copolymers include, without limitation, those set forth in Table 3.

TABLE 3

| Tetronic ® | Form | HLB | Average MW |
|---|---|---|---|
| 304 | Liquid | 16 | 1650 |
| 701 | Liquid | 3 | 3600 |
| 704 | Liquid | 15 | 5500 |
| 901 | Liquid | 3 | 4700 |
| 904 | Liquid | 15 | 6700 |
| 908 | Solid | 31 | 25000 |
| 1107 | Solid | 24 | 15000 |
| 1301 | Liquid | 2 | 6800 |
| 1307 | Solid | 24 | 18000 |
| 90R4 | Liquid | 7 | 7240 |
| 150R1 | Liquid | 1 | 8000 |

In selecting PEO-PPO copolymers for use in the instant invention, the poly(oxyethylene) units making up the first segment need not consist solely of ethylene oxide as previously mentioned. Nor is it necessary that all of the poly(oxypropylene) segment consist solely of propylene oxide units. Instead, in the simplest cases, for example, at least one of the monomers in segment A may be substituted with a side chain group.

In addition, the present invention can also be practiced using diamine-linked polyoxyethylene-polyoxypropylene polymers of formula:

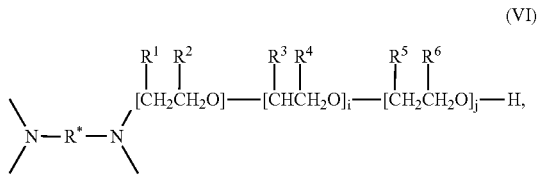

(VI)

wherein the same number and sequence of polyether moieties extend symmetrically from each nitrogen; i and j have values from about 2 to about 800, preferably from about 5 to about 200, more preferably from about 5 to about 80; R* is an alkylene of about 2 to about 6 carbons, a cycloalkylene of about 5 to about 8 carbons or phenylene; $R^1$ and $R^2$, either (a) both represent hydrogen or (b) one represents hydrogen and the other represents methyl; $R^3$ and $R^4$ either (a) both are hydrogen or (b) one is hydrogen and the other is methyl; if both of $R^3$ and $R^4$ represent hydrogen, then one of $R^5$ and $R^6$ represents hydrogen and the other is methyl; and both of $R^5$ and $R^6$ represent hydrogen when one of $R^3$ and $R^4$ represents methyl.

Over 30 Pluronic® copolymers with different lengths of hydrophilic ethylene oxide ($N_{EO}$) and hydrophobic propylene oxide ($N_{PO}$) blocks are available from BASF Corp. (see, for example, Tables 2 and 4). These molecules are characterized by different hydrophilic-lipophilic balance (HLB) and CMC (Kozlov et al. (2000) Macromolecules, 33:3305-3313; see, for example, Tables 3 and 4). The HLB value, which typically falls in the range of 1 to 31 for Pluronic® block copolymers, reflects the balance of the size and strength of the hydrophilic groups and lipophilic groups of the polymer (see, for example, Attwood and Florence (1983) "Surfactant Systems: Their Chemistry, Pharmacy and Biology," Chapman and Hall, New York) and can be determined experimentally by, for example, the phenol titration method of Marszall (see, for example, "Parfumerie, Kosmetik", Vol. 60, 1979, pp. 444-448; Rompp, Chemistry Lexicon, 8th Edition 1983, p. 1750; U.S. Pat. No. 4,795,643). HLB values for Pluronic® polymers are available from BASF Corp. HLB values can be approximated by the formula:

$$HLB = -36\frac{y}{2x+y} + 33,$$

wherein y is the number of hydrophobic propylene oxide units and x is the number of hydrophilic ethylene oxide units, though HLB values provided by BASF are preferred. Notably, as hydrophobicity increases, HLB decreases.

TABLE 4

| Pluronic ® | MW[a] | $N_{PO}$[b] | $N_{EO}$[b] | HLB[a] | CMC, µM[c] |
|---|---|---|---|---|---|
| L31 | 1100 | 17.1 | 2.5 | 5 | 1180 |
| L35 | 1900 | 16.4 | 21.6 | 19 | 5260 |
| F38 | 4700 | | | 31 | |
| L42 | 1630 | | | 8 | |
| L43 | 1850 | 22.3 | 12.6 | 12 | 2160 |
| L44 | 2200 | 22.8 | 20.0 | 16 | 3590 |
| L61 | 2000 | 31 | 4.5 | 3 | 110 |
| L62 | 2500 | 34.5 | 11.4 | 7 | 400 |
| L63 | 2650 | | | 11 | |
| L64 | 2900 | 30 | 26.4 | 15 | 480 |
| P65 | 3400 | | | 17 | |
| F68 | 8400 | 29 | 152.7 | 29 | 480 |
| L72 | 2750 | | | 7 | |

TABLE 4-continued

| Pluronic® | MW[a] | $N_{PO}$[b] | $N_{EO}$[b] | HLB[a] | CMC, μM[c] |
|---|---|---|---|---|---|
| P75 | 4150 | | | 17 | |
| F77 | 6600 | | | 25 | |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.3 | 10.0 | 1 | 1 |
| L122 | 5000 | | | 4 | |
| P123 | 5750 | 69.4 | 39.2 | 8 | 44 |
| F127 | 12600 | 65.2 | 200.4 | 22 | 2.8 |
| 10R5 | 1950 | | | 15 | |
| 10R8 | 4550 | | | 19 | |
| 12R3 | 1800 | | | 7 | |
| 17R1 | 1900 | | | 3 | |
| 17R2 | 2150 | | | 6 | |
| 17R4 | 2650 | | | 12 | |
| 17R8 | 7000 | | | 16 | |
| 22R4 | 3350 | | | 10 | |
| 25R1 | 2700 | | | 2 | |
| 25R2 | 3100 | | | 4 | |
| 25R4 | 3600 | | | 8 | |
| 25R5 | 4250 | | | 10 | |
| 25R8 | 8550 | | | 13 | |
| 31R1 | 3250 | | | 1 | |
| 31R2 | 3300 | | | 2 | |
| 31R4 | 4150 | | | 7 | |

[a]The average molecular weights and HLB provided by the manufacturer (BASF Co.);
[b]The average numbers of EO and PO units were calculated using the average molecular weights of the blocks;
[c]Critical micelle concentration (CMC) values at 37° C. were determined using pyrene probe (Kozlov et al. (2000) Macromolecules, 33: 3305-3313).

The transport of non-conjugated Pluronic® copolymers in brain microvessel endothelial cells depends on the hydrophobicity of the block copolymers (Batrakova et al. (2003) J. Pharmacol. Exp. Ther., 304:845-854). Copolymers, with intermediate hydrophobicity, such as P85 (HLB=16), are easily transported inside the cells. The most hydrophobic copolymers, such as L121 (HLB=1), may remain bound with the membrane structures. Additionally, the relatively hydrophilic copolymers (HLB>20) may not readily penetrate cells. Notably, following conjugation with polypeptides, the transport characteristics of the conjugates may not match exactly those of the unconjugated block copolymer molecules alone. Thus, the hydrophobicity/lipophilicity of the protein prior to conjugation may be taken into account when selecting a polymer to conjugate to the protein.

Preferably, the amphiphilic polymer of the instant invention is a copolymer of poly(oxyethylene) and poly(oxypropylene), more preferably the amphiphilic polymer is a Pluronic® copolymer. The preferred amphiphilic polymer possesses an HLB of less than or equal to 20, with an HLB of less than or equal to 16 being more preferred, with an HLB of less than or equal to 12 being more preferred and an HLB of less than or equal to 8 being most preferred. The amphiphilic polymers also preferably contain long hydrophobic blocks, wherein the molecular weight of the hydrophobic block is preferably greater than 1500, with a hydrophobe weight of greater than 2000 being more preferred, with a hydrophobe weight of greater than 2500 being even more preferred, and with a hydrophobe weight of greater than 3000 being most preferred.

III. Proteins

While the preferred embodiment of the instant invention involves conjugating proteins to the amphiphilic polymers in order to mediate crossing of a biological membrane, it is also within the scope of the instant invention to conjugate other therapeutic agents or compounds of interest to the amphiphilic polymer. Such agents or compounds include, without limitation, polypeptides, peptides, nucleic acids, synthetic and natural drugs, and lipids.

In a preferred embodiment of the instant invention, the proteins conjugated to the amphiphilic polymers are therapeutic proteins, i.e., they effect amelioration and/or cure of a disease, disorder, pathology, and/or the symptoms associated therewith. The proteins may have therapeutic value against, without limitation, neurological degenerative disorders, stroke, Alzheimer's disease, Parkinson's disease, gliomas, cancers, HIV, HIV associated dementia, paralysis, obesity, and lysosomal diseases (such as, without limitation, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), and Fabry disease). Examples of specific proteins include, without limitation, cytokines, enkephalin, growth factors (e.g., epidermal growth factor (EGF), basic fibroblast growth factor (bFGF), nerve growth factor (NGF)), amyloid beta binders (e.g. antibodies), modulators of α-, β-, and/or γ-secretases, Glial-derived neutrotrophic factor (GDNF), vasoactive intestinal peptide, acid alpha-glucosidase (GAA), acid sphingomyelinase, iduronate-2-sultatase (I2S), α-L-iduronidase (IDU), β-Hexosaminidase A (HexA), Acid β-glucocerebrosidase, N-acetylgalactosamine-4-sulfatase, α-galactosidase A. Certain of the proteins are exemplified in Table 5.

TABLE 5

| Protein | Ref. | Disease | Function |
|---|---|---|---|
| Glial-derived neutrotrophic factor (GDNF) | Schapira, A. H. (2003) Neurology 61: S56-63 | Parkinson's and Alzheimer's diseases Stroke | Neuroprotection and neurorestoration |
| Epidermal growth factor (EGF) | Ferrari, G., et al. (1990) Adv Exp Med Biol. 265: 93-99 | Parkinson's and Alzheimer's diseases Stroke | Stimulates dopaminergic development |
| Basic fibroblast growth factor (bFGF) | Ferrari, G., et al. (1991) J Neurosci Res. 30: 493-497 | Parkinson's and Alzheimer's diseases Stroke | Stimulates proliferation and migration of neutral stem cells |
| Nerve growth factor (NGF) | Koliatsos, V. E., et al. (1991) Ann Neurol. 30: 831-840 | Parkinson's and Alzheimer's diseases Stroke | Protects cholinergic cells from injury-induced death |
| Vasoactive intestinal peptide | Dogrukol-Ak, D., et al. (2003) Peptides 24: 437-444 | Alzheimer's diseases Stroke | Promote neuronal survival, prevent exitotoxic cell death |

TABLE 5-continued

| Protein | Ref. | Disease | Function |
|---|---|---|---|
| Acid alpha-glucosidase (GAA) | Amalfitano, A., et al. (2001) Genet Med. 3: 132-138 | Pompe (lysosomal disease) | Enzyme replacement therapy |
| Acid sphingomyelinase | Simonaro, C. M., et al. (2002) Am J Hum Genet. 71: 1413-1419 | Niemann-Pick (lysosomal disease) | Enzyme replacement therapy |
| Iduronate-2-sultatase (I2S) | Muenzer, J., et al. (2002) Acta Paediatr Suppl. 91: 98-99 | Hunter syndrome (MPS II) (lysosomal disease) | Enzyme replacement therapy |
| α-L-iduronidase (IDU) | Wraith, J. E., et al. (2004) J Pediatr. 144: 581-588 | Mucopolysaccharidosis I (MPS I) (lysosomal disease) | Enzyme replacement therapy |
| β-Hexosaminidase A (HexA) | Wicklow, B. A., et al. (2004) Am J Med Genet. 127A: 158-166 | GM2-gangliosidoses (lysosomal disease) | Enzyme replacement therapy |
| Acid β-glucocerebrosidase | Grabowski, G. A., (2004) J Pediatr. 144: S15-19. | Gaucher disease (lysosomal disease) | Enzyme replacement therapy |
| N-acetylgalactosamine-4-sulfatase | Auclair, D., et al. (2003) Mol Genet Metab. 78: 163-174 | Sanfilippo syndrome (MPS IIIA) (lysosomal disease) | Enzyme replacement therapy |
| α-galactosidase A | Przybylska, M., et al. (2004) J Gene Med. 6: 85-92 | Fabry (lysosomal disease) | Enzyme replacement therapy |

Additionally, the therapeutic protein optionally does not exhibit any appreciable therapeutic activity prior to cleavage/removal of the linker and/or amphiphilic polymer. In other words, prior to cleavage the therapeutic protein does not produce its intended therapeutic effect.

IV. Linkers

Exemplary linkers and methods of conjugating the linker with the protein of interest and the amphiphilic polymer are provided in Example 4. The linker moiety joining the amphiphilic polymer and the protein of the conjugate is preferably biodegradable. In a preferred embodiment, the linker is cleaved in vivo as the conjugate either passes through the BBB, or upon completion of the transfer across the BBB. In a certain embodiment of the instant invention, the linker moiety comprises amino acids that constitute a protease recognition site or other such specifically recognized enzymatic cleavage site. Exemplary protease recognition sites include, without limitation, amino acid sequences cleavable by endosomal cathepsin, such as cathepsin B (e.g., Gly-(Phe)-Leu-Gly (SEQ ID NO: 1); see, e.g., DeNardo et al. (2003) Clinical Cancer Res. 9:3865s-72s); sequences cleavable by lysosomal proteases (e.g., Gly-Leu-Gly (SEQ ID NO: 2) and Gly-Phe-Leu-Gly (SEQ ID NO: 1); see, e.g., Guu et al. (2002) J. Biomater. Sci. Polym. Ed. 13:1135-51; Rejmanova et al. (1985) Biomaterials 6:45-48); and sequences cleavable by collagenase (e.g., GGGLGPAGGK (SEQ ID NO: 3) and KALGQPQ (SEQ ID NO: 4); see, e.g., Gobin and West (2003) Biotechnol. Prog. 19:1781-5; Kim and Healy (2003) Biomacromolecules 4:1214-23).

In another embodiment the linker region comprises a disulfide bond. Preferably, the disulfide bond is stable in the blood, but hydrolyzable by reductases present in the BBB. Representative examples of linker moieties comprising a disulfide bond include, without limitation:

—OC(O)NH(CH$_2$)$_2$NHC(O)(CH$_2$)$_2$SS(CH$_2$)$_2$C(O)NH—;

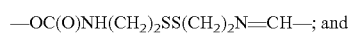
—OC(O)NH(CH$_2$)$_2$SS(CH$_2$)$_2$N═CH—; and

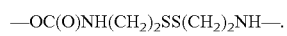
—OC(O)NH(CH$_2$)$_2$SS(CH$_2$)$_2$NH—.

In another embodiment the linker region comprises a hydrolyzable ester. Preferably, the hydrolyzable ester is stable in the blood, but hydrolyzable by hydrolases present in the BBB.

In a preferred embodiment, the linker moiety is completely cleaved or substantially cleaved, effecting the removal of the amphiphilic polymer from the protein. In yet another embodiment, the linker moiety is completely cleaved or substantially cleaved resulting in the removal of the amphiphilic polymer from the protein and most, if not all, of the linker region.

Additionally, the linkage between the protein and the amphiphilic polymer can be a direct linkage between a functional group at a termini of the polymer and a functional group on the protein.

V. Administration of Conjugates

The amphiphilic polymer-protein conjugates described herein will generally be administered to a patient as a pharmaceutical preparation. The term "patient" as used herein refers to human or animal subjects. These amphiphilic polymer-protein conjugates may be employed therapeutically, under the guidance of a physician.

The pharmaceutical preparation comprising the amphiphilic polymer-protein conjugates of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of amphiphilic polymer-protein conjugates in the chosen medium will depend on the hydrophobic or hydrophilic nature of the medium, as well as the size and other properties of the amphiphilic polymer-protein conjugates. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding discussion. The use of such media for pharmaceutically active substances is known in the art. Except insofar as any conventional media or agent is incompatible with the amphiphilic polymer-protein conjugate to be administered, its use in the pharmaceutical preparation is contemplated.

The dose and dosage regimen of an amphiphilic polymer-protein conjugate according to the invention that is suitable for administration to a particular patient may be determined by a physician considering the patient's age, sex, weight, general medical condition, and the specific condition for which the amphiphilic polymer-protein conjugate is being administered and the severity thereof. The physician may also take into account the route of administration of the amphiphilic polymer-protein conjugate, the pharmaceutical carrier with which the amphiphilic polymer-protein conjugate is to be combined, and the amphiphilic polymer-protein conjugate's biological activity.

Selection of a suitable pharmaceutical preparation will also depend upon the mode of administration chosen. For example, the amphiphilic polymer-protein conjugates of the invention may be administered by direct injection into an area proximal to the BBB. In this instance, a pharmaceutical preparation comprises the amphiphilic polymer-protein conjugates dispersed in a medium that is compatible with the site of injection.

Amphiphilic polymer-protein conjugates may be administered by any method such as intravenous injection into the blood stream, oral administration, or by subcutaneous, intramuscular or intraperitoneal injection. Pharmaceutical preparations for injection are known in the art. If injection is selected as a method for administering the amphiphilic polymer-protein conjugates, steps must be taken to ensure that sufficient amounts of the molecules reach their target cells to exert a biological effect. The lipophilicity of the amphiphilic polymer-protein conjugates, or the pharmaceutical preparation in which they are delivered, may have to be increased so that the molecules can arrive at their target location. Furthermore, the amphiphilic polymer-protein conjugates may have to be delivered in a cell-targeting carrier so that sufficient numbers of molecules will reach the target cells. Methods for increasing the lipophilicity of a molecule are known in the art.

Pharmaceutical compositions containing a conjugate of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, direct injection, intracranial, and intravitreal. In preparing the amphiphilic polymer-protein conjugate in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which solid pharmaceutical carriers are employed. If desired, tablets may be sugar-coated or enteric-coated by standard techniques. Injectable suspensions may also be prepared, in which case appropriate liquid carriers, suspending agents and the like may be employed. Additionally, the conjugate of the instant invention may be administered in a slow-release matrix. For example, the conjugate may be administered in a gel comprising unconjugated poloxamers.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of amphiphilic polymer-protein conjugates may be determined by evaluating the toxicity of the molecules in animal models. Various concentrations of amphiphilic polymer-protein conjugate pharmaceutical preparations may be administered to mice, and the minimal and maximal dosages may be determined based on the beneficial results and side effects observed as a result of the treatment. Appropriate dosage unit may also be determined by assessing the efficacy of the amphiphilic polymer-protein conjugate treatment in combination with other standard drugs. The dosage units of amphiphilic polymer-protein conjugate may be determined individually or in combination with each treatment according to the effect detected.

The pharmaceutical preparation comprising the amphiphilic polymer-protein conjugates may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The following examples provide illustrative methods of practicing the instant invention, and are not intended to limit the scope of the invention in any way. While certain of the following examples specifically identify a certain type of Pluronic® block copolymer (e.g., Pluronic® P85), the use of any amphiphilic polymer is within the scope of the instant invention.

Example 1

Generation of Pluronic®-Amines

The conjugates of Pluronic® copolymers can be synthesized by first generating mono-amino derivatives of Pluronic® copolymers, which are referred to herein as "Pluronic®-amines." The "Pluronic®-amines" were generated as described in Vinogradov et al. (Bioconjug. Chem. (1998) 9:805-812). Essentially, the method of Vinogradov et al. is a two step procedure.

First, 2 to 3 g of Pluronic® (L81, P85, L121 and P123) were dried overnight in vacuo at 50° C. and then dissolved in 15 ml of anhydrous acetonitrile. One molar equivalent of 4'-methoxytrityl chloride (MTr-Cl) were dissolved in 10 ml of anhydrous pyridine and added to the Pluronic® solution. Acetonitrile was then removed in vacuo, and the mixture was allowed to stand for 3 hours at 25° C. The reaction was then stopped by adding 1 ml of methanol, and pyridine was removed in vacuo by co-evaporation with 2×15 ml of toluene. The monosubstituted MTr-Pluronic® was isolated from non-reacted polymer and bis-MTr-Pluronic® by adsorption chromatography on Silicagel column (4.5×10 cm) using dichloromethane-methanol stepwise gradient elution. The products were then analyzed by thin-layer chromatography (TLC) in chloroform-MeOH, 9:1, and detected in trifluoroacetic acid vapors (test to the presence of MTr-group). Product yields were typically 70-85% of theoretical.

In the second step, 1-1.5 g of mono-MTr-Pluronic® was dried by co-evaporation with 2×15 ml of anhydrous acetonitrile in vacuo and then reacted with 5-fold molar excess of 1,1'-carbonyldiimidazole (CDI) in 10 ml of anhydrous acetonitrile for 1 hour at 40° C. The reaction mixture was then treated with 0.2 ml of water for 20 min to neutralize the unreacted CDI, and then added to a solution of ethylenediamine (20-fold molar excess) in 40 ml of ethanol upon stirring. The mixture was kept overnight at 25° C., diluted by 50 ml of water and dialyzed for 18 hours using a membrane with 2,000 kDa cutoff against 10% aqueous ethanol (2×2 L). After the dialysis, the polymer was concentrated in vacuo, co-evaporated twice with methanol (10 ml), and re-dissolved in 50 ml of 2% trifluoroacetic acid (TFA) in dichloromethane. After incubation for 1 hour at 25° C., the bright yellow solution was concentrated in vacuo and neutralized by 5 ml of 10% triethylamine in methanol. The resulting Pluronic®-amine was isolated by gel filtration on Sephadex LH-20 column (2.5×30 cm) and analyzed by TLC in chloroform-MeOH, 9:1, mixture. The Pluronic®-amines develop blue color after spraying with 1% ninhydrine solution in ethanol (as a test for the presence of an aminogroup). The product yields were about 70-80% of theoretical. About 85 to 95% of Pluronic® molecules contain primary amino groups as determined by 2,4,6-trinitrobenzolsulfonic acid (TNBS) titration.

The TNBS titration can be performed as follows. A 5% solution of TNBS (Sigma-Aldrich, St. Louis, Mo.) was diluted 100 times in 1M Na-borate buffer, pH 9.5. The native and modified compounds were dissolved in the same buffer at 1 mg/ml. The reaction was then initiated by adding the compound and TNBS solutions (20 µl each) to 180 µl of 0.1M Na-borate buffer, pH 9.5 in 96-well plates. After a 1 hour incubation at 20° C., the optical density (405 nm) was recoded on a Microplate reader, in triplicate. The number of modified groups per protein is determined as $S=N \times (1-A_m C_n/A_n C_m)$, where N is the number of primary aminogroups in the native compound, $A_n$ and $A_m$ are the optical densities for the native and modified compounds, and $C_n$ and $C_m$ are the concentrations of native and modified compounds, as determined, for example, by the Pierce BCA assay (Rockford, Ill.) using dilutions a standard BSA solution for calibration.

Example 2

Conjugation of Pluronic®-Amines with Proteins

Figure 1:
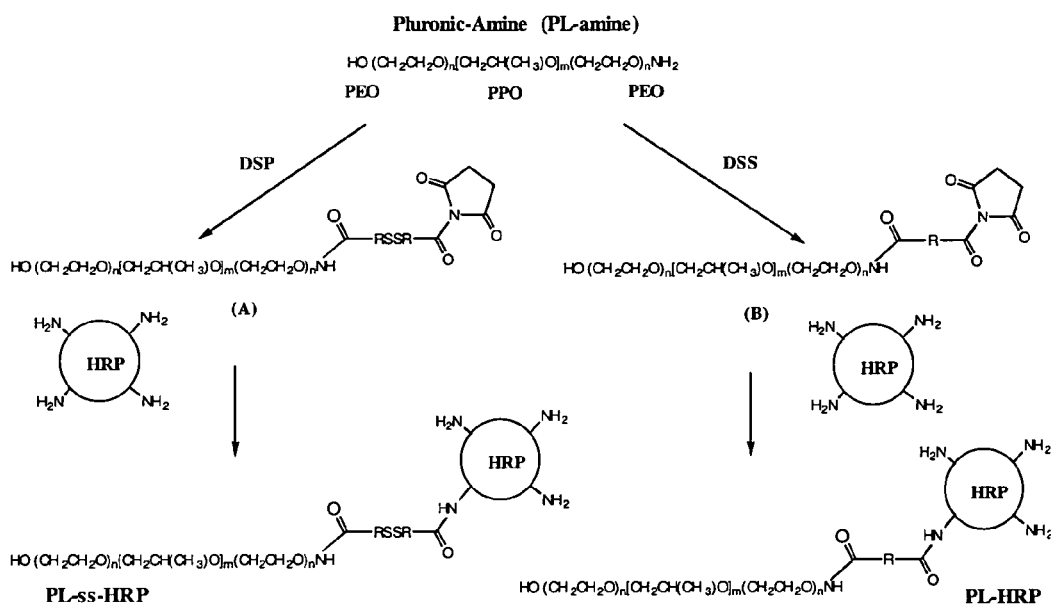

"Pluronic®-Amine" derivatives, as obtained in Example 1, were then conjugated to horseradish peroxidase (HRP) using the two-step procedure shown in FIG. 1. HRP was chosen as a lead model for these experiments because its size of 40 kDa is similar to molecules of therapeutic interest and because its BBB characteristics are well known. HRP does not cross the BBB by saturable or transmembrane mechanisms. Only a small amount enters brain from the circulation by way of the extracellular pathways, which are the same pathway used by albumin. In other words, it essentially does not penetrate the BBB.

In the first step of the conjugation procedure, Pluronic®-amines were activated with Loman's reagent, dithiobis(succinimidyl propionate) (DSP), or disuccinimidylsuberate (DSS). Specifically, Pluronic®-amine (50-70 µmol) in 2.5 ml of methanol was added dropwise to a stirred solution of 3-fold molar excess of dithiobis(succinimidyl propionate) (DSP) to generate a cleavable linker or disuccinimidyl suberate (DSS) for a nondegradable, stable linker, in 2.5 ml of dimethylformamide and kept for 30 min at 25° C. The resulting hydroxysuccinimide derivatives of Pluronic® were isolated by gel filtration on Sephadex LH-20 column (2.5×30 cm) in methanol and analyzed by TLC developed in iodine vapors.

Figure 2A:
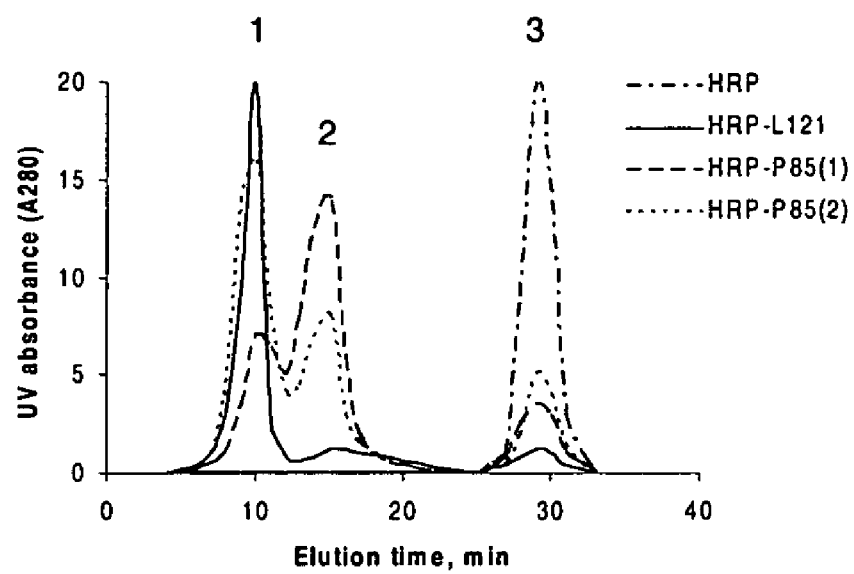
Figure 2B:
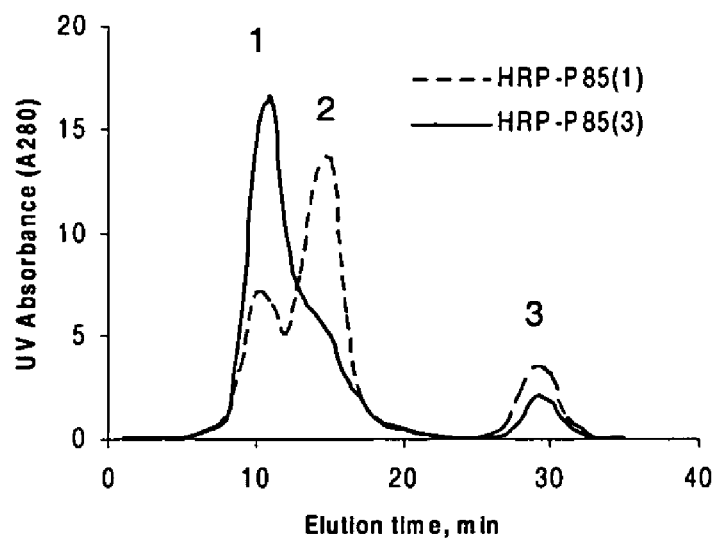

Second, the products of the above reactions were linked to the aminogroups of HRP. The DSP reagent was used to introduce a cleavable or degradable disulfide linkage between the HRP and Pluronic® molecules, while the DSS linkage was not degradable. Specifically, pooled fractions were collected, concentrated in vacuo, and dissolved in 1.5 ml of 20% ethanol. HRP (1 µmol) was dissolved in 0.5 ml of 0.1 M borate buffer, pH 9.5, and mixed with a previously prepared solution (1.5 ml) of activated Pluronic® to a obtain total volume of 2 ml. The homogeneous reaction mixture was kept overnight at 4° C. Modified HRP was then precipitated in 50 ml of cold ethanol (−10° C., 0.5 hour), and separated from the excess of polymer by centrifugation at 3000 rpm for 20 min at 4° C. Yellow precipitate was washed by cold ethanol (2×10 ml) and dried in vacuo. Pluronic®-HRP conjugate was purified by cation exchange chromatography using glass column (1×15 cm) with TSK CM-650M resin. Pluronic®-HRP conjugate was eluted in 50 mM sodium acetate, pH 4.4, 0.03M sodium chloride and 2.5% ethanol with detection at 280 nm (FIGS. 2A and 2B). Residual unmodified HRP was eluted in a gradient of the sodium chloride (0.03 to 0.15M). Collected fractions were desalted in dialysis tubes with 20 kDa cutoff against water at 4° C. and freeze-dried.

To vary the number of copolymer chains per protein molecule, different excesses of activated Pluronic® were used. Overall, four conjugates with stable or degradable linkages and different modification degrees were synthesized as shown in Table 6. TNBS analysis demonstrated that the products contained mainly mono- and bis-substituted protein. The fractions of unmodified HRP did not exceed 25%. The unmodified HRP was discarded, while the fractions of modified protein (peaks 1 and 2) were combined for each conjugate and used in subsequent studies. The characteristics of the Pluronic®-HRP conjugates obtained are summarized in Table 6.

TABLE 6

| Conjugate | Pluronic ® excess | Type of link | Modification degree[a] | Residual activity, %[b] |
|---|---|---|---|---|
| HRP-P85 (1) | 50 | degradable | 1.4 | 97 |
| HRP-P85 (2) | 50 | stable | 1.6 | 100 |
| HRP-P85 (3) | 70 | degradable | 2.0 | 89 |
| HRP-L121 | 70 | degradable | 2.1 | 95 |

[a]Average number of Pluronic ® chains per HRP molecule determined using TNBS titration assay.
[b]Compared to the native HRP, o-phenylenediamine reaction.

Example 3

Alternative Methods for Generating Pluronic®-Polypeptide Conjugates

Figure 3:
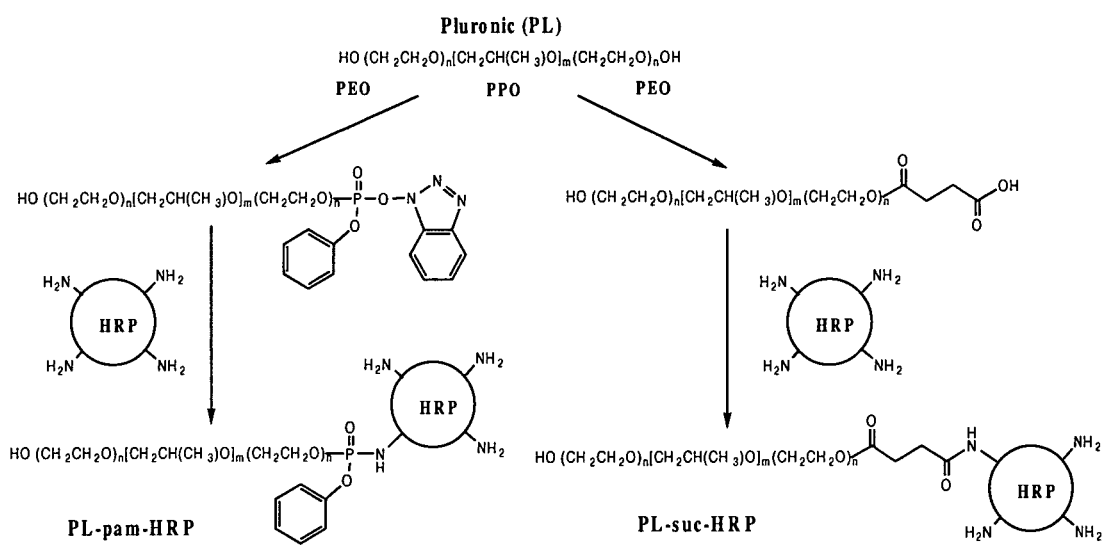

Two alternative methods for introduction of degradable linkages in Pluronic®-polypeptide conjugates are presented in FIG. 3. In both methods Pluronic® can be taken in excess to avoid activation of both ends.

One method involves the introduction of a phosphoramidate linkage, which is susceptible to a mild acidic hydrolysis in endosomes following the cleavage of phosphomonoester group within the cells (Wagner et al. (2000) Med. Res. Rev. 20:417-451). Bis-(N-hydroxybenzotriazolyde)-phenylphosphate can be generated in situ by reacting dichlorophenylphosphate (30 μmol), N-hydroxybenzotriazole (60 μmol) and diisopropylethylamine (60 μmol) in 5 ml of anhydrous THF for 1 hour at 4° C. This reagent can be added dropwise to a stirred solution of excess of Pluronic® (90 μmol, dried overnight in vacuo at 50° C.) in 5 ml of THF and the mixture can be kept for 4 hours at 25° C. The activated Pluronic® can be isolated from unreacted block copolymer by gel filtration on Sephadex LH-20 column (2.5×30 cm) in methanol and analyzed by TLC developed by exposure to iodine vapors. Pooled fractions can be concentrated in vacuo, and dissolved in 1.5 ml of 20% ethanol before reaction with polypeptides.

The second method involves preparation of succinate-Pluronic® derivative, which is then conjugated to HRP using water soluble carbodiimide. Notably, the ester bond is hydrolytically degradable (Wagner et al. (2000) Med. Res. Rev. 20:417-451). A solution of succinic anhydride/dimethylaminopyridine (30 μmol:3 μmol) in 1 ml of anhydrous pyridine can be added dropwise to a stirred solution of excess of Pluronic® (90 μmol) in 5 ml of THF and the mixture can be kept overnight at 25° C. The solvent can be removed in vacuo. The activated Pluronic® can be purified by gel filtration on Sephadex LH-20 column (2.5×30 cm) in methanol and analyzed by TLC. Pooled fractions can be concentrated in vacuo, and dissolved in 1.5 ml of 20% ethanol and used for reaction with HRP (4-6 h, 25° C.) in the presence of a 3 molar equivalents of ethyl dimethylaminopropyl carbodiimide.

Example 4

Examples of Pluronic®-Protein Conjugate Preparations

The following are examples of synthetic procedures for the preparation of Pluronic®-protein conjugates with degradable linkers. The last example provides methods used to characterize the resultant conjugates. Method 1 gives outlines of monosubstituted methoxytrityl Pluronic® and the synthesis of five types of monofunctional polymers (Pluronic®) including linkers with the following structures:
  (1) Polymer-OC(O)NH(CH$_2$)$_2$NH$_2$
  (2) Polymer-OC(O)NH(CH$_2$)$_2$SS(CH$_2$)$_2$NH$_2$
  (3) Polymer-OC(O)(CH$_2$)$_2$COOH
  (4) Polymer-OP(O)(OPh)OH
  (5) Polymer-OC(O)NH(CH$_2$)$_2$NHC(O)CH$_2$C(OH)(COOH)CH$_2$COOH Methods 2-6 enable the generation of Pluronic®-protein conjugates having the following structures:
  (1) Polymer-OC(O)NH(CH$_2$)$_2$NHC(O)(CH$_2$)$_2$SS(CH$_2$)$_2$C(O)NH-Protein
  (2) Polymer-OC(O)NH(CH$_2$)$_2$SS(CH$_2$)$_2$N=CH-Protein
  (3) Polymer-OC(O)(CH$_2$)$_2$C(O)NH-Protein
  (4) Polymer-OP(O)(OPh)NH-Protein
  (5) Polymer-OC(O)NH(CH$_2$)$_2$NHC(O)CH$_2$C(OH)(COOH)CH$_2$C(O)NH-Protein Method 1. Synthesis of Monofunctional Pluronic® Block Copolymers 1. Monosubstituted methoxytrityl Pluronic®. 3 g of Pluronic® was dried in vacuo at 50° C. and then dissolved in 15 mL of anhydrous acetonitrile. One molar equivalent of methoxytrityl chloride (Aldrich) was dissolved in 10 mL of anhydrous pyridine and added to the Pluronic® solution. Acetonitrile was removed by evaporation in vacuo and the mixture was allowed to stand for 3 hours at 25° C. The reaction was stopped by adding 1 mL of methanol and pyridine was removed in vacuo by coevaporating twice with 15 mL of toluene. The monosubstituted product was isolated from non-reacted polymer and by products using adsorption chromatography on a Silicagel column (4.5×10 cm) in dichloromethane. Stepwise gradient elution with dichloromethane and 2%, 5%, and 10% methanol in dichloromethane (150 mL each) was used, and fractions of 8 mL were collected. Yields: 2.5-3 g (70-85% of theoretical). Thin layer chromatography (TLC): $R_f$ 0.6 (Silicagel plates (Merck, Whitehouse Station, N.J.), dichloromethane-methanol, 9: 1). The product developed yellow coloring on the TLC plate in acid vapors (test on the presence of methoxytrityl group).

2. Monosubstituted Pluronic® ethylamine. The monosubstituted methoxytrityl Pluronic® was dried in vacuo over phosphorus oxide and treated by 5 molar equivalents of 1,1'-carbonyldiimidazole (CDI) (Aldrich, St. Louis, Mo.) in 10 mL of anhydrous acetonitrile for 2 hours at 40° C. Water (0.2 mL) was added to quench the excess of CDI, and 20 min later, this solution was added to a 40 mL of stirring 10% solution of ethylenediamine in ethanol. The reaction mixture was stirred overnight at 25° C. and then was diluted by the same volume of water (50 mL). Low molecular weight compounds have been removed by dialysis in the membrane tube with cutoff 2,000 in 2 L of 10% aqueous ethanol for 18 hours at 4° C. with two changes of the solution. The dialysate was concentrated in vacuo and redissolved in 50 mL of 2% trifluoroacetic acid in dichloromethane. Following the incubation for 1 hour at 25° C., bright yellow solution was concentrated in vacuo and neutralized by 5 mL of 10% triethylamine in methanol. The monosubstituted Pluronic® ethylamine was isolated by gel filtration on Sephadex LH20 column (2.5×30 cm) in methanol collecting fractions: 8 mL/4 min. Yields: 2.0-2.2 g of white solids (70-80% of theoretical). TLC: $R_f$ 0.4 (Silicagel plates, dichloromethane-methanol, 9:1). The product developed blue color after spraying the TLC plates with 1% ninhydrine solution in ethanol, to test for the presence of amino group.

3. Monosubstituted Pluronic®-cystamine. The monosubstituted methoxytrityl Pluronic® was dried in vacuo over phosphorus oxide and treated by 5 molar equivalents of 1,1'-carbonyldiimidazole (CDI) in 10 mL of anhydrous acetonitrile for 2 hours at 40° C. Water (0.2 mL) was added to quench the excess of CDI, and 20 min later, this solution was added to a 40 mL of stirring 20% solution of cystamine, in the form of free amine, in ethanol. The reaction mixture was stirred overnight at 25° C. and then was diluted by the same volume of water (50 mL). Low molecular weight compounds were been removed by dialysis in the membrane tube with cutoff 2,000 in 2 L of 10% aqueous ethanol for 18 hours at 4° C. with two changes of the solution. The dialysate was concentrated in vacuo and redissolved in 50 mL of 2% trifluoroacetic acid in dichloromethane. Following the incubation for 1 hour at 25° C., bright yellow solution was concentrated in vacuo and neutralized by 5 mL of 10% triethylamine in methanol. The monosubstituted Pluronic® cystamine was isolated by gel filtration on Sephadex LH 20 column (2.5×30 cm) in methanol collecting fractions: 8 mL/4 min. Yields: 2.0-2.2 g of white solids (70-80% of theoretical). TLC: $R_f$ 0.4 (Silicagel plates, dichloromethane-methanol, 9:1). The product developed blue color after spraying the TLC plates with 1% ninhydrine solution in ethanol.

4. Monosubstituted Pluronic® succinate. The monosubstituted methoxytrityl Pluronic® was dried in vacuo over phosphorus oxide and treated by 5 molar equivalents of succinic anhydride (Aldrich) in 10 mL of anhydrous pyridine in the presence of catalytic quantity of 4-dimethylaminopyridine for 4 hours at 40° C. Methanol (0.5 mL) was added to quench the excess of reagent for 30 min at 25° C. Low molecular weight compounds have been removed by dialysis in the membrane tube with cutoff 2,000 in 2 L of 10% aqueous ethanol for 18 hours at 4° C. with two changes of the solution. The dialysate was concentrated in vacuo and redissolved in 50 mL of 2% trifluoroacetic acid in dichloromethane. Following the incubation for 1 hour at 25° C., bright yellow solution was concentrated in vacuo and neutralized by 5 mL of 10% triethylamine in methanol. The monosubstituted Pluronic®-succinate was isolated by gel filtration on Sephadex LH-20 column (2.5×30 cm) in methanol collecting fractions: 8 mL/4 min. Yields: 2.4-2.5 g of white solids (>85% of theoretical). TLC: $R_f$ 0.3 (Silicagel plates, dichloromethane-methanol, 9:1).

5. Monosubstituted Pluronic® phenylphosphate. The monosubstituted methoxytrityl Pluronic® was dried in vacuo over phosphorus oxide and treated by 2 molar equivalents of phenyl phosphorodichloridate in the presence of 2.2 equivalents of diisopropylethylamine in 20 mL of anhydrous dioxane for 1 hour in an ice bath. Then an excess of 1% aqueous hydrochloric acid (100 mL) was added and the reaction mixture was stirred for 1 hour at 25° C. After adjusting pH to 7, low molecular weight compounds have been removed by dialysis in the membrane tube with cutoff of 2,000 in 2 L of 10% aqueous ethanol for 18 hours at 4° C. with two changes of the solution. The monosubstituted Pluronic® phenylphosphate was freeze-dried. Yields: 2.0 g of white solids (70% of theoretical). TLC: $R_f$ 0.25 (Silicagel plates, dichloromethane-methanol, 9:1).

6. Monosubstituted Pluronic® citrate. For modification of Pluronic® block copolymer with citric acid, 330 mg of Pluronic®-amine was first dissolved in 2.5 mL of methanol and added dropwise to a stirring solution of 110 mg of citric acid incubated with 55 mg of N,N' dicyclohexylcarbodiimide in 5 mL of DMF for 1 hour at 25° C. Following the 4 hour reaction, the modified Pluronic® was isolated by gel filtration on Sephadex LH 20 column (2.5×30 cm) in methanol (fractions 8 mL/4 min). Yields: 0.3 g of white solids (90% of theoretical). TLC: $R_f$ 0.35 (Merck Silicagel plates, dichloromethane methanol, 9:1).

Method 2. Synthesis of Protein Conjugate with Pluronic® Ethylamine (DSP Method)

For activation of Pluronic® block copolymer, 330 mg of Pluronic® amine was first dissolved in 2.5 mL of methanol and added dropwise to a stirring solution of 80 mg of dithiobis (succinimidyl) propionate (DSP) in 2.5 mL of DMF at 25° C. Following the 30 min reaction, the DSP modified Pluronic® was isolated by gel filtration on Sephadex LH 20 column (2.5×30 cm) in methanol (fractions 8 mL/4 min). TLC: $R_f$ 0.5-0.6 (Merck Silicagel plates, dichloromethane-methanol, 9:1). The product developed yellow color after exposure of TLC plates to iodine vapors (test on the presence of Pluronic® polymers). Polymer-containing fractions were collected and concentrated in vacuo. The N-hydroxysuccinimidocarboxyl (NHS) product (Pluronic®-NHS) was dissolved in 1.5 mL of 20% ethanol immediately before reaction with protein.

44 mg of horseradish peroxidase (HRP type VI, MW 44 KDa; Sigma, St. Louis, Mo.) was dissolved in 0.5 mL of 0.1 M borate, pH 9.5, and mixed with a previously prepared solution (1.5 mL) of Pluronic®-NHS to obtain total volume of 2 mL. Homogeneous reaction mixture was kept overnight at 4° C. Modified HRP was precipitated in 40 mL of cold (−10° C.) ethanol, incubated in a refrigerator for 30 min, and separated from excess of Pluronic®-NHS by centrifugation at 3000 rpm for 20 min at 4° C. Brown precipitate was washed by cold ethanol (2×10 ml) and dried in vacuo. Yield: 75-90 mg.

Pluronic®-HRP conjugate was purified by cation exchange chromatography using glass column (2×8 cm) with TSK CM-650M resin in 10 mM sodium acetate, pH 4.4, 10 mM sodium chloride and 5% ethanol at elution rate 1.5 mL/min. First, the column was washed by this eluent, and then elution with sodium chloride (gradient from 0.01 to 0.15M over 60 min) was used for isolation of the Pluronic®-HRP and separation of residual (unreacted) HRP. Collected fractions were desalted in dialysis tubes with a cutoff of 20 KDa against water overnight at 4° C. and freeze-dried. The obtained conjugate was analyzed by protein and salt contents using the analytical procedures described below.

Method 3. Synthesis of Protein Conjugate with Pluronic® Cystamine (Periodate Method)

To a solution of 44 mg of horseradish peroxidase (Sigma, HRP type VI) in 1 mL of water, 50 µl, of freshly prepared 0.1 M aqueous solution of sodium metaperiodate was added to oxidize the vicinal hydroxyl groups of carbohydrate moieties of HRP and generate HRP-aldehyde. The reaction mixture was vortex mixed and kept for 30 min at 25° C. in the dark. Activated HRP (HRP-aldehyde) was passed through a small NAP-20 column previously equilibrated with 10 mM ammonium carbonate, pH 9.3, to remove excess of metaperiodate. The brown colored fraction of activated HRP was directly collected in a vial containing 300 mg of Pluronic®-cystamine dissolved in the above buffer (2 ml); the reaction mixture was vortex mixed and kept overnight at 4° C. to form a Schiff base. After overnight incubation, 50 µL of 5 M sodium cyanoborohydride was added, and reaction mixture was vortex mixed and kept for 3 h at 4° C. The solution was degassed and passed through a Sephadex G-25 column (2.5×30 cm) previously equilibrated with 10 mM PBS. The brown colored fractions containing Pluronic®-HRP conjugate were collected, desalted and purified by cation exchange chromatography as described above. Isolated Pluronic®-HRP conjugate was desalted and freeze dried. Yield: 85-90 mg. The conjugate was analyzed by protein and salt contents using the analytical procedures described below.

Method 4. Synthesis of Protein Conjugate with Pluronic® Succinate

For activation of Pluronic® block copolymer, 330 mg of Pluronic®-succinate and 50 mg of N-hydroxysuccinimide were first dissolved in 5 mL of dry dioxane, then 45 mg of N,N'-dicyclohexylcarbodiimide (DCC) added to the solution at 25° C. Following the overnight reaction, an N-hydroxysuccinimidocarboxyl Pluronic® derivative (Pluronic®-NHS) was isolated by gel filtration on Sephadex LH-20 column (2.5×30 cm) in methanol (fractions 8 mL/4 min). TLC: $R_f$ 0.7 (Merck Silicagel plates, dichloromethane-methanol, 9:1). The product developed yellow color after exposure of TLC plates to iodine vapors (test on the presence of Pluronic® polymers). Polymer containing fractions were collected and concentrated in vacuo. The product was dissolved in 1.5 mL of 20% ethanol immediately before reaction with protein.

44 mg of horseradish peroxidase (Sigma, HRP type VI) was dissolved in 0.5 mL of 0.1 M borate, pH 9.5, and mixed with a previously prepared solution (1.5 mL) of Pluronic®-NHS to obtain total volume of 2 mL. Homogeneous reaction mixture was kept overnight at 4° C. Modified HRP was precipitated in 40 mL of cold (−10° C.) ethanol, incubated in a refrigerator for 30 min and separated from excess of Pluronic®-NHS by centrifugation at 3000 rpm for 20 min at 4° C. Brown precipitate was washed by cold ethanol (2×10 ml) and dried in vacuo. Yield: 80-100 mg.

Pluronic®-HRP conjugate was purified by cation exchange chromatography using glass column (2×8 cm) with TSK CM-650M resin in 10 mM sodium acetate, pH 4.4, 10 mM sodium chloride and 5% ethanol at elution rate 1.5 mL/min. First, the column was washed by this eluent, and then elution with sodium chloride (gradient from 0.01 to 0.15M over 60 min) was used for isolation of the Pluronic®-HRP and separation of residual (unreacted) HRP. Collected fractions were desalted in dialysis tubes with a cutoff 20 KDa against water overnight at 4° C. and freeze-dried. The obtained conjugate was analyzed by protein and salt contents using the analytical procedures described below.

Method 5. Synthesis of Protein Conjugate with Pluronic® Phenylphosphate 330 mg of Pluronic®-phenylphosphate and 60 mg of 1 hydroxybenzotriazole were dissolved in 5 ml of aqueous dioxane, and 40 mg of ethyl diisopropylaminocarbodiimide (EDC) was added to the solution at 25° C. The reaction was performed for 4 hours at 25° C. and the hydroxybenzotriazole-modified Pluronic® (Pluronic®-HBT) was isolated by gel filtration on Sephadex LH-20 column (2.5×30 cm) in methanol (fractions 8 ml/4 min). The product developed yellow color after exposure of TLC plates to iodine vapors (test on the presence of Pluronic® polymers). Polymer containing fractions were collected and concentrated in vacuo. The product was dissolved in 1.5 mL of 20% ethanol immediately before reaction with protein.

44 mg of horseradish peroxidase (Sigma, HRP type VI) was dissolved in 0.5 mL of 0.1 M borate, pH 9.5, and mixed with a previously prepared solution (1.5 mL) of Pluronic® HBT to obtain total volume of 2 mL. Homogeneous reaction mixture was kept overnight at 4° C. Modified HRP was precipitated in 40 mL of cold (-10° C.) ethanol, incubated in refrigerator for 30 min and separated from excess of Pluronic®-HBT by centrifugation at 3000 rpm for 20 min at 4° C. Brown precipitate was washed by cold ethanol (2×10 ml) and dried in vacuo. Yield: 80-100 mg.

Pluronic® HBT conjugate was purified by cation exchange chromatography using a glass column (2×8 cm) with TSK CM-650M resin in 10 mM sodium acetate, pH 4.4, 10 mM sodium chloride and 5% ethanol at elution rate 1.5 mL/min. First, the column was washed by this eluent, and then elution with sodium chloride (gradient from 0.01 to 0.15 M over 60 min) was used for isolation of the Pluronic®-HBT and separation of residual (unreacted) HBT. Collected fractions were desalted in dialysis tubes with a cutoff of 20 KDa against water overnight at 4° C. and freeze-dried. The obtained conjugate was analyzed by protein and salt contents using the analytical procedures described below.

Method 6. Synthesis of Protein Conjugate with Pluronic® Citrate 300 mg of Pluronic®-citrate and 50 mg of N-hydroxysuccinimide were first dissolved in 5 mL of dry dioxane, then 45 mg of N,N'-dicyclohexylcarbodiimide added to the solution at 25° C. Following the overnight reaction, an N-hydroxysuccinimidocarboxyl Pluronic® derivative (Pluronic®-citrate-NHS) was isolated by gel filtration on Sephadex LH-20 column (2.5×30 cm) in methanol (fractions 8 mL/4 min). TLC: $R_f$ 0.7 (Merck Silicagel plates, dichloromethane-methanol, 9:1). The product developed yellow color after exposure of TLC plates to iodine vapors. Polymer containing fractions were collected and concentrated in vacuo. The product was dissolved in 1.5 mL of 20% ethanol immediately before reaction with protein.

44 mg of horseradish peroxidase (Sigma, HRP type VI) was dissolved in 0.5 mL of 0.1 M borate, pH 9.5, and mixed with a previously prepared solution (1.5 mL) of Pluronic®-citrate-NHS to obtain total volume of 2 mL. Homogeneous reaction mixture was kept overnight at 4° C. Modified HRP was precipitated in 40 mL of cold (-10° C.) ethanol, incubated in refrigerator for 30 min and separated from excess of Pluronic®-NHS by centrifugation at 3000 rpm for 20 min at 4° C. Brown precipitate was washed by cold ethanol (2×10 ml) and dried in vacuo. Yield: 70-85 mg.

Pluronic®-citrate-HRP conjugate was purified by cation exchange chromatography using glass column (2×8 cm) with TSK CM-650M resin in 10 mM sodium acetate, pH 4.4, 10 mM sodium chloride and 5% ethanol at elution rate 1.5 mL/min. First, the column was washed by this eluent, and then elution with sodium chloride (gradient from 0.01 to 0.15M over 60 min) was used for isolation of the Pluronic®-citrate-HRP and separation of residual (unreacted) HRP. Collected fractions were desalted in dialysis tubes with a cutoff of 20 KDa against water overnight at 4° C. and freeze-dried. The obtained conjugate was analyzed by protein and salt contents using the analytical procedures described below.

Method 7. Analysis of Pluronic® Protein Conjugates

1. Protein Assay. Pierce BCA Kit was used to measure protein content in the Pluronic® conjugates. Protein sample was dissolved in water (1.0 mg/mL). Standard solutions of bovine serum albumin (BSA) have been used to obtain calibration curve. Three parallel aliquots were taken per sample and each standard solution. The kit's Solution A (10 mL) was mixed with the kit's Solution B (0.2 mL, 1150 dilution), then 0.02 mL of sample solution and 0.2 mL of summary mixture AB were added into 96 well plate by multi channel pipette (8 tips). Mixtures were incubated for 30 min at 37° C., and an absorbance of purple solutions was measured at 550 nm. Results were compared with calibration curve to calculate the protein content.

2. Pluronic®/protein molar ratio. The Pluronic®/protein molar ratio was determined by substitution rate of amino groups in protein. Solutions of initial and modified protein (1 mg/ml) were first prepared. Commercial 5% solution of 2,4,6 trinitrobenzosulfonic acid (TNBS) (Sigma) was dissolved in 100 times by 0.1M Na-borate buffer, pH 9.5, before analysis. Reaction was performed with 20 µL of sample and 20 µL of TNBS solution in 160 µL of 0.1 M Na borate buffer, pH 9.5, in 96 well plate. Three parallel aliquots were taken per each sample. Reaction mixtures were incubated for 1 h at 25 C, and an absorbance of brown solutions was determined at 405 nm in Microplate reader. HRP contains 6 primary amino groups. To calculate the substitution rate, the amino group content (A) was divided by protein content (N). The following equation calculates the number of polymer molecules per protein $S_i = 4N_0(A_0N_0 - A_i/N_i)/A_0$.

3. HRP enzymatic activity. Samples (20 µL) with protein concentration 0.1 mg/mL obtained by dilution of initial solutions (1 mg/mL) in 10,000 times by water were taken in 96 well plate. 200 µL of the solution of o-phenylenediamine (5 mg/mL) in 0.1 M citrate buffer, pH 5, containing 1 mg/mL BSA, 0.1% Triton and 0.02% of hydrogen peroxide was used as color substrate in reaction for 5 min at 37° C. 30 µL of a Stop solution (0.5% sodium sulphite dissolved in a 2 N sulfuric acid) was immediately added, and absorbance measured at 450 550 nm to determine the HRP activity. Calibration curve for HRP activity per mg of protein was plotted and used in these calculations.

Example 5

Binding of Pluronic®-HRP Conjugates to Brain Endothelial Cells

Figure 4:
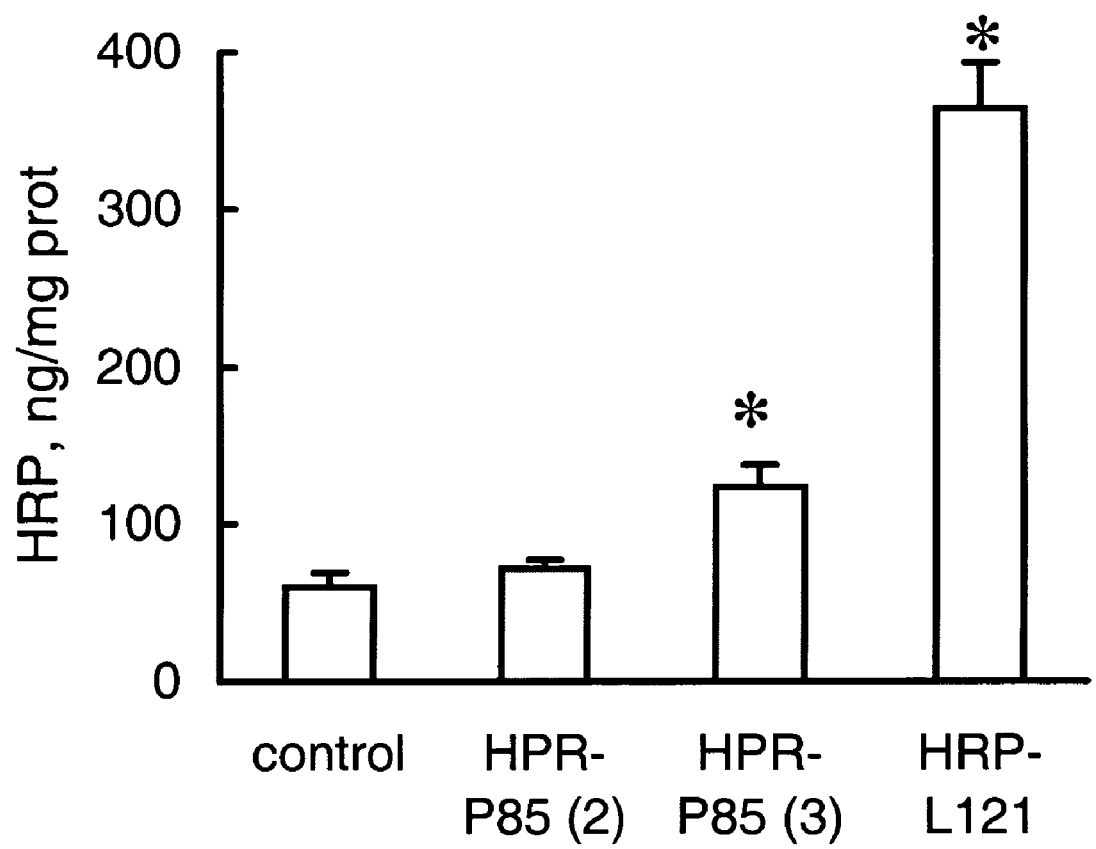
FIG. 4 is a bar graph of the level of binding of unmodified HRP and Pluronic® HRP conjugates, described in Table 6 below, with BBMEC monolayers in 60 min. Data are mean±SEM (n=4). (*) indicates significant difference compared to HRP.

FIG. 4 summarizes the results of the study of binding of various Pluronic®-HRP conjugates with bovine brain microvessel endothelial cell (BBMEC) monolayers. The primary cultured BBMEC retain many of the morphological and biochemical characteristics of the BBB and display transport systems present in vivo (Miller et al. (1992) J. Tissue Cult. Methods, 14:217-224). These cells form tight junctions and possess low pinocytic activity and therefore possess low permeability for macromolecules, including unmodified HRP (Karyekar et al. (2003) J. Pharm. Sci., 92:414-423). At the same time, these cells express receptor systems that enable transcellular transport (transcytosis) of selected macromolecules (Miller et al. (1994) J. Cell. Physiol., 161:333-341; Maresh et al. (2001) Life Sci., 69:67-73). Thus, primary cultured BBMEC are well suited for identifying and characterizing the transport processes in the BBB at the cellular level.

BBMECs were isolated from cow brains, obtained at a local meat processing plant, using mechanical and enzymatic disruption of brain matter coupled with gradient separation as described in Miller et al. (J. Tissue Cult. Methods (1992) 14:217-224). Cells were seeded onto either 1) collagen coated, fibronectin-treated 24-well culture plates at a density of 50,000 cells/cm$^2$ or 2) polycarbonate membrane inserts, 24-mm, 0.4 μm pore size (Fisher Scientific, Pittsburgh, Pa.) at a density of 250,000 cells/insert. The cells were grown using media consisting of 45% minimum essential medium (MEM), 45% Ham's F-12 (F12), and 10% horse serum supplemented with antibiotics and heparin sulfate and used after reaching confluency (typically 10-12 days).

The BBMECs were incubated with unmodified HRP or the conjugates for 60 min. The cell monolayers were washed with 1% bovine serum albumin (BSA) in phosphate buffered saline (PBS) and then washed in PBS. Notably, the experiments can be conducted with and without 10% fetal calf serum to assess possible effects of serum binding on the transport of the modified HRP. The cells were then lysed in 1% Triton X100 and the net amount of the cell-bound enzyme was determined by calorimetric reaction with o-phenylenediamine in 0.1M citrate buffer containing 0.1% Triton X100, 1 mg/ml BSA, and 0.02% hydrogen peroxide. The amount of HRP was normalized by the amount of cell protein as determined by the Pierce BCA assay.

There was little difference in binding of unmodified HRP and HRP-P85(2) conjugate, containing a stable linkage. However, the binding of conjugates containing a cleavable disulfide linkage (HRP-P85(3) and HRP-L121) was increased significantly. The most pronounced effect (over 6-fold increase of binding) was observed in the case of a hydrophobic Pluronic® L121 conjugate. This result was consistent with the earlier report suggesting strong binding of this hydrophobic block copolymer with the BBMEC membranes (Batrakova et al. (2003) J. Pharmacol. Exp. Ther., 304:845-854). HRP-P85(3) displayed about a 2-fold increase in binding with the cells. Therefore, modification of HRP with Pluronic® can increase the overall binding of this protein with brain microvessel endothelial cells.

Example 6

Permeability of Pluronic®-HRP in BBMEC Monolayers

The following study evaluated permeability of various Pluronic®-HRP conjugates in BBMEC monolayers. The method entailed radioactively labeling the native or modified polypeptides with $^{125}$I using Iodobeads (Pierce, Rockford, Ill.) and purifying by Sephadex G10 column chromatography. Confluent BBMEC monolayers were grown on polycarbonate membrane inserts placed in Side-Bi-Side diffusion cells from Crown BioScientific, Inc. (Somervile, N.J.) and maintained at 37° C.±0.1° C. and preincubated with an assay buffer (122 mM NaCl, 25 mM NaHCO$_3$, 10 mM glucose, 3 mM KCl, 1.2 mM MgSO$_4$, 0.4 mM K$_2$HPO$_4$, 1.4 mM CaCl$_2$ and 10 mM HEPES) for 30 min. The confluent monolayers mean resistance was no less than 120.0 Ω·cm$^2$. For luminal to abluminal transport studies, the assay buffer at the luminal (apical) side was removed and replaced with the transport buffer containing solutions of the modified or native polypeptides radioactively labeled with $^{125}$I (10$^6$ cpm) Notably, the experiments can be conducted with and without 10% fetal calf serum to assess possible effects of serum binding on the transport of the modified HRP. The aliquots at the abluminal (basolateral) side of the monolayers was removed at 15, 30, 45, 60, 90 and 120 min and immediately replaced with the same volume of the assay buffer. The radioactivity was measured in a gamma counter. In the case of HRP, the enzyme activity was also measured using o-phenylenediamine as a substrate to determine activity of the protein. All transport experiments were conducted in triplicate. The trans-epithelial electrical resistance (TEER) of the monolayers was recorded as an index of cell viability and monolayer integrity. At the end of the experiment, the monolayers were solubilized in 0.5 ml of 1% Triton X100 and the amount of cell associated radioactivity was measured along with the radioactivity from solutions in donor and receiver chambers. The liquid samples were precipitated by 30% trifluoroacetic acid (TFA) and the radioactivity in the pellet and supernatant was determined. The percent of the intact material was defined as [cpm pellet/(cpm pellet+cpm supernatant)]×100%.

Figure 5:
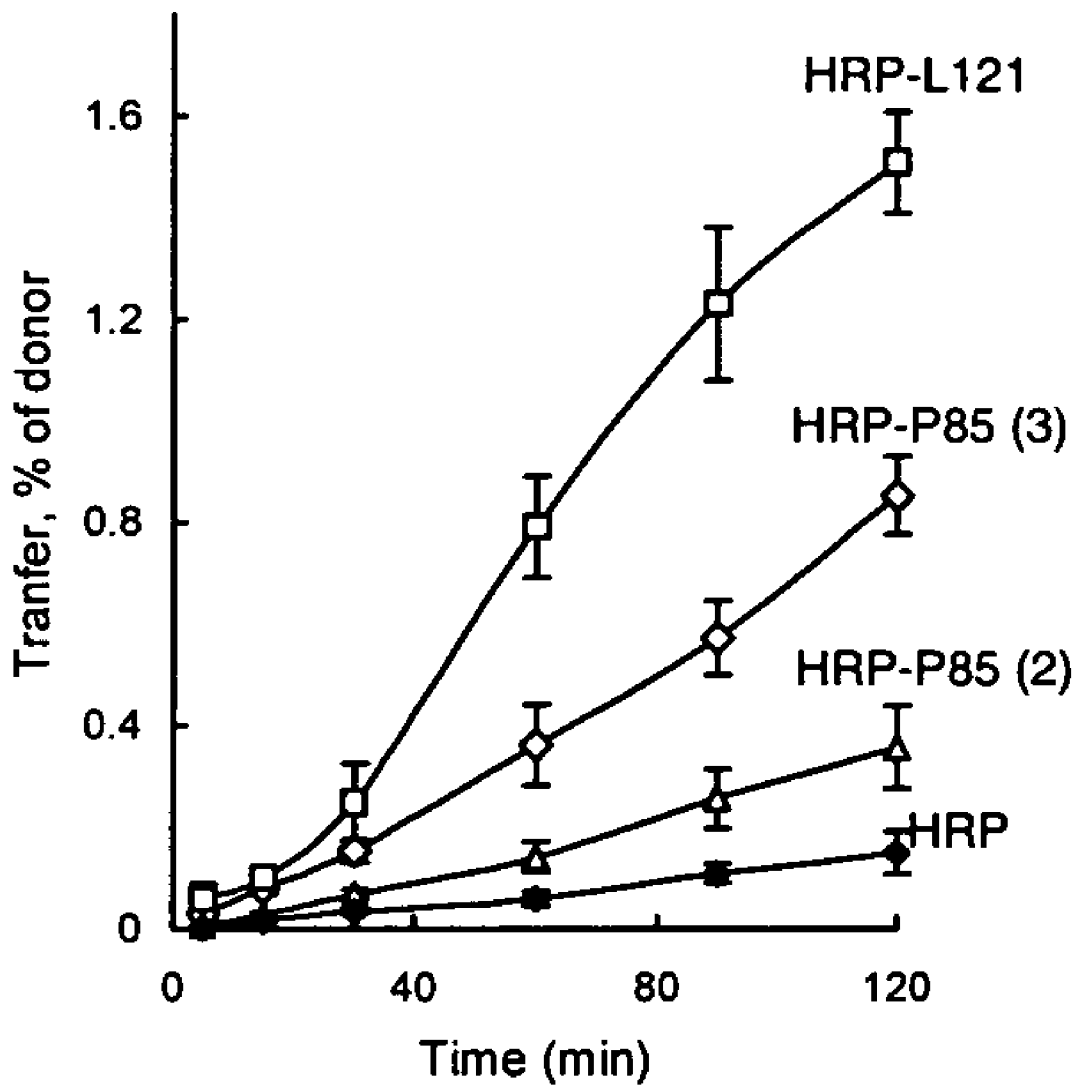
FIG. 5 is a graph demonstrating the apical to basolateral permeability of HRP and Pluronic®-HRP in BBMEC monolayers as a function of time. Data are mean±SEM (n=4).

Notably, neither the conjugated nor unmodified HRP caused alteration in TEER suggesting that the integrity of the monolayer's tight junctions was not affected. At the same time there were substantial differences in permeability displayed by different conjugates. The transport of unmodified HRP was quite slow. Modification of HRP with P85 via non-degradable linkage (HRP-P85 (2)) resulted in approximately two-fold increase in the permeability of the protein (FIG. 5). The conjugate containing the cleavable linkage, HRP-P85 (3), was transported almost six times fasted than the unmodified HRP (FIG. 5). Finally, the conjugate with the hydrophobic Pluronic® L121, also containing a cleavable linkage, displayed the highest rates of transport across the BBMEC monolayers (FIG. 5). The rate of its transport was over 10-times higher than that of the unmodified HRP. Overall, the conjugation of the enzyme with highly hydrophobic Pluronic® L121 via the biodegradable linkage resulted in the greatest increase in permeability across the brain endothelial cells.

Example 7

Microviscosity Studies in BBMEC

To examine effects of Pluronic®s on the fluidity properties of the cell plasma membranes in BBMEC, a fluorescent compound, 1 [4(trimethylamino)phenyl]-6-phenylhexa-1,3,5-triene (TMA DPH) was used (Prendergast et al. (1967) Biochemistry, 20:7333-7338). For these studies, the BBMEC suspension was incubated with various Pluronic® conjugates for 2 hours at 37° C., washed twice and incubated with 2 μM TMA-DPH (Molecular Probes, Eugene, Oreg.) for 10 minutes. Then, the cells were washed twice to remove extracellular probe, and re-suspended in an appropriate volume of PBS and changes in fluorescent polarization were recorded.

Fluorescence intensities were measured with a Hitachi F5000 spectrophotometer equipped with a polarizer set. This instrument detects fluorescence intensity (I) with the relative position of the polarizer and analyzer (parallel, $I_\|$, or perpendicular, $I\perp$) and fluorescence anisotropy r, was calculated according to Eq. 1:

$$r=(I_\|-I\perp)/=(I_\|+2I\perp)$$

An excitation wavelength of 365 nm and an emission wavelength of 425 nm were used for both probes. Cell suspensions were gently mixed before each reading. In all cases, corrections for stray light and intrinsic fluorescence were made by subtracting the values for III and Ii, of unlabeled samples from those of identical but labeled samples. Microviscosities (η) were derived as described previously TMA-DPH (Chazotte, B. (1994) Biochim. Biophys. Acta., 1194:315-328) by the method based on the Perrin equation (Eq. 2) for rotational depolarization of a nonspherical fluorophore:

$$r_0/r=1+C(r)\tau/\eta$$

where $r_0$ and r are limiting and measured fluorescence anisotropies, T is the absolute temperature, and τ is the exited state lifetime. The value of $r_0$ and τ were 0.362 and 7 ns, respectively. C(r) is a molecular shape parameter equal to $15.3\times10^5$ poise·deg$^{-1}$s$^{-1}$.

Figure 6:
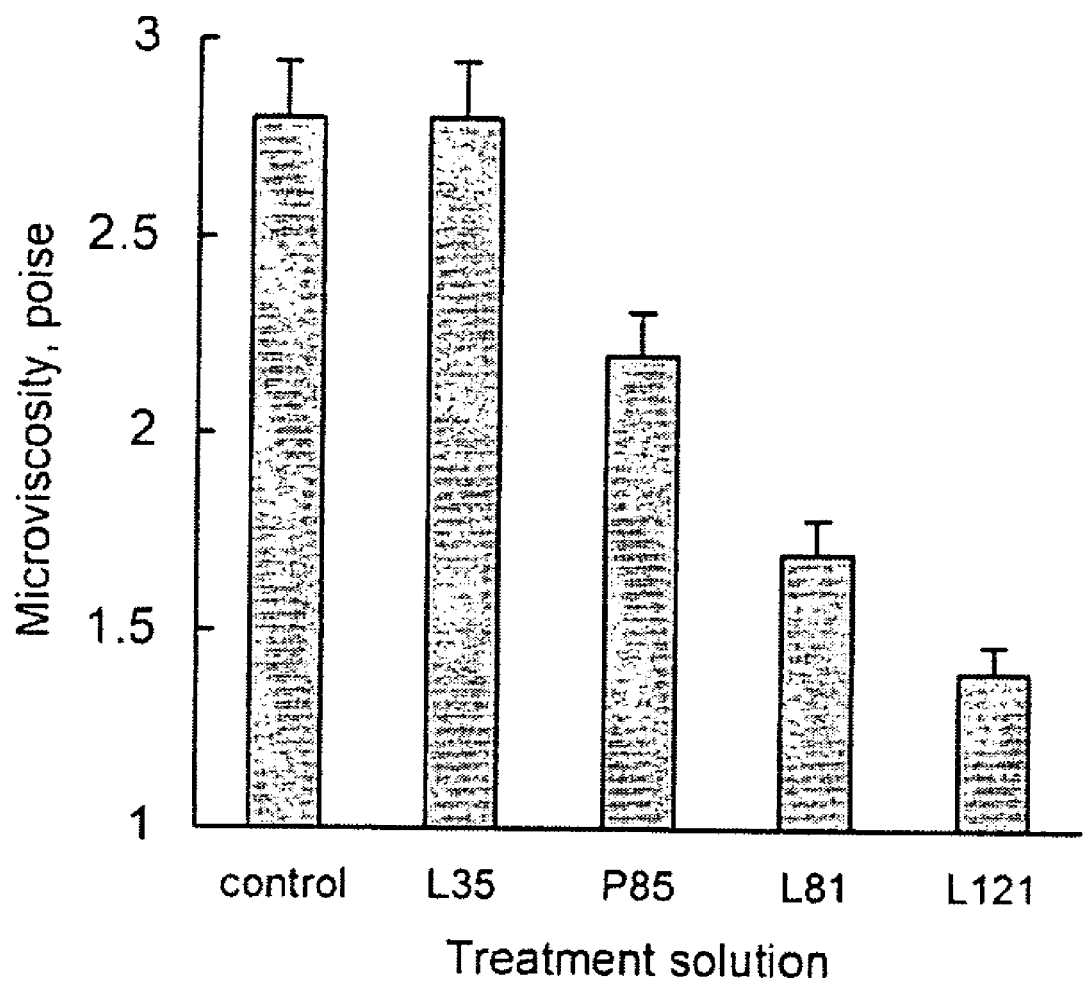
FIG. 6 is a bar graph showing the effects of various Pluronic® copolymers on the viscosity of BBMEC monolayers.

The obtained results suggest that more lipophilic PBC have stronger fluidization effect on BBMEC membranes (FIG. 6).

Example 8

Fatty Acid Conjugates

Artificial hydrophobization of polypeptides with a small number of fatty acid residues (e.g. stearate or palmitate) has been shown to enhance cellular uptake (Kabanov et al. (1989) Protein Eng. 3:39-42). Specifically, this approach involves point modification of lysine or N-terminal amino groups with one or two fatty acid residues per protein molecule. As a result of such modification the protein molecule remains water-soluble but also acquires hydrophobic anchors that can target even very hydrophilic proteins to cell surfaces (Slepnev et al. (1995) Bioconjug. Chem. 6:608-615). Fatty acid modification of water-soluble polypeptides, such as HRP, results in enhanced polypeptide binding with the cell membranes and internalization in many cell types (Slepnev et al. (1995) Bioconjug. Chem. 6:608-615).

Previous studies have shown that modification of the Fab fragments of antibodies against gliofibrillar acid protein (GFAP) and brain specific alpha 2-glycoprotein (alpha 2GP) with stearate led to an increased accumulation of the modified Fab fragments in the brain in a rat (Chekhonin et al. (1991) FEBS Lett. 287:149-152; Chekhonin et al. (1995) Neuroreport. 7:129-132). Furthermore, a neuroleptic drug conjugated with the stearoylated antibody Fab fragments was much more potent compared to the free drug. In comparison, fatty acylated Fab fragments of non-specific antibodies did not accumulate in the brain but instead accumulated in the liver, while stearoylated Fab fragments of brain-specific antibodies displayed preferential accumulation in the brain. Subsequent studies using bovine brain microvessel endothelial cells (BBMEC) as an in vitro model of BBB demonstrated that stearoylation of ribonuclease A (approx. 13.6 kDa) increases the passage of this enzyme across the BBB by almost 8.8-fold (Chopineau et al. (1998) J. Control Release 56:231-237). Of the three fatty acid derivatives analyzed—myristic, palmitic and stearic, the latter was the most active. A possible mechanism for the entry of the fatty acylated polypeptides to the brain is adsorptive endocytosis. Given the characteristics of the BBB transport for nonessential free fatty acids as reviewed elsewhere, it is unlikely that the modified polypeptides are able to use those transporters (Banks et al. (1997) Permeability of the blood-brain barrier to circulating free fatty acids. in: Handbook of Essential Fatty Acid Biology: Biochemistry, Physiology, and Behavioral Neurobiology, pp. 3-14 (Yehuda, S. and Mostofsky, D. I., Eds.) Humana Press, Totowa, N.J.). Thus, use of free fatty acid receptor mediated transport by the modified polypeptides is not likely. However, essential fatty acids, such as linoleic, are more readily transported (Edmond, J. (2001) J. Mol. Neurosci. 16:181-193; discussion 215-221; Edmond et al. (1998) J. Neurochem. 70:1227-1234).

While stearic acid is exemplified herein, the instant invention contemplates the conjugation of essential fatty acids directly or through a cleavable linker to the protein to be transported across the BBB.

The enzyme horseradish peroxidase (HRP) contains six amino groups available for chemical modification. To modify these groups with stearic acid residues, the enzyme was acylated with stearoyl chloride in the reverse micelle system of Aerosol OT in octane (Slepnev et al. (1995) Bioconjug. Chem. 6:608-615). Based on the titration of the remaining free amino groups of the protein with 2,4,6-trinitrobenzene-sulfonic acid, an average of 1.1 stearic acid residue per protein molecule was introduced onto HRP under these conditions. The solubility of the stearoylated HRP (St-HRP) was about 1 mg/ml, its RZ was 2.7 and the catalytic activity—50% of the native HRP activity (RZ of native HRP—3.0).

The effect of stearic acid acylation on the HRP overall binding with brain endothelial cells was studied using primary bovine brain microvessel edothelial cells (BBMEC) as an in vitro model of the BBB. Briefly, the BBMEC monolayers were grown to confluency (10-13 days), and then exposed for various times to the solutions of unmodified or stearoylated HRP (St-HRP) (40 µg/ml). After that the cell monolayers were washed (with 1% bovine serum albumin (BSA) in phosphate buffered saline (PBS), and then in PBS) and lysed in 1% Triton X100. The HRP activity in the lysates was determined by calorimetric reaction with o-phenylenediamine in 0.1 M-citrate buffer, containing 0.1% Triton X-100, 1 mg/ml BSA, and 0.02% hydrogen peroxide. The amount of the HRP was normalized by the cell protein determined using the Pierce-BCA assay. The results are presented in FIG. 7A. Modification of HRP resulted in about a 3 fold increase of its overall binding with the BBMEC.

BBMEC monolayers grown to confluency on membrane inserts were placed in Side-Bi-Side diffusion cells. The unmodified or St-HRP (40 µg/ml) was placed in the donor chamber at the apical side of the monolayers. The appearance of the enzyme in the receiver chamber at the basolateral side of the monolayers was registered by measuring the activity of HRP. The trans-epithelial electrical resistance (TEER) of the monolayers was recorded as an index of cell viability and monolayer integrity. As shown in FIG. 7B, modification increased the apparent permeability coefficient ($P_{app}$) about 2-fold ($0.4\times10^8$ cm/s) when compared with the non-modified HRP ($0.24\times10^8$ cm/s). There were no changes in TEER or permeability of a paracellular marker, $^3$H-mannitol, demonstrating that the integrity of the monolayers was not altered.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for delivering a therapeutic agent across the blood-brain barrier into the central nervous system of an animal comprising administering to said animal a conjugate comprising said therapeutic agent conjugated to an amphiphilic block copolymer by a cleavable linker moiety, said cleavable linker moiety linker comprising a disulfide bond.

2. The method of claim 1, wherein said therapeutic agent is a protein.

3. The method of claim 2, wherein said amphiphilic block copolymer is a copolymer comprising at least one poly(oxyethylene) segment and at least one poly(oxypropylene) segment.

4. The method of claim 3, wherein said amphiphilic block copolymer has a formula selected from the group consisting of:

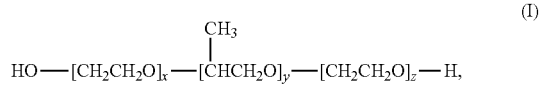

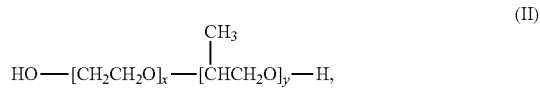

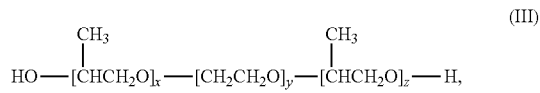

-continued

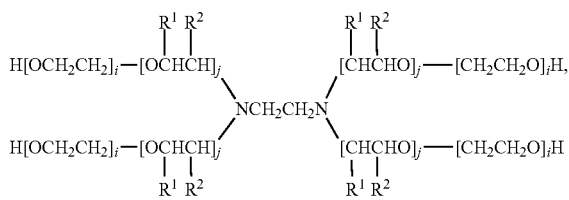

(IV)

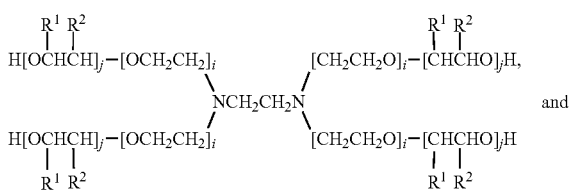

(V)

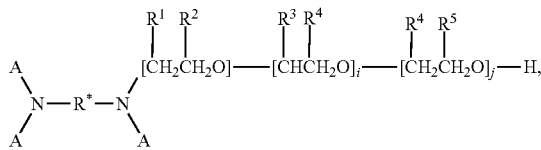

(VI)

wherein x, y, z, i, and j have values from about 2 to about 800; wherein in formulas (IV) and (V), for each R¹ and R² pair one is hydrogen and the other is a methyl group; wherein in formula (VI), R* is an alkylene of about 2 to about 6 carbons, a cycloalkylene of about 5 to about 8 carbons, or phenylene; R¹ and R² are either both represent hydrogen or one represents hydrogen and the other represents methyl; R³ and R⁴ are either both are hydrogen or one is hydrogen and the other is methyl; if both of R³ and R⁴ represent hydrogen, then one of R⁵ and R⁶ represents hydrogen and the other is methyl; if one of R³ and R⁴ represents methyl, then both R⁵ and R⁶ represent hydrogen; and A represents

5. The method of claim 4, wherein said amphiphilic block copolymer is of the formula:

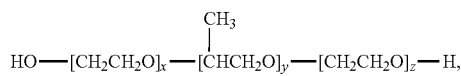

wherein x, y, and z have values from about 2 to about 800.

6. The method of claim 5, wherein x, y, and z have values from about 5 to about 80.

7. The method of claim 6, wherein x+z=10 and y=68.

8. The method of claim 3, wherein said amphiphilic block copolymer has a hydrophilic-lipophilic balance (HLB) of less than or equal to 20.

9. The method of claim 8, wherein said amphiphilic block copolymer has an HLB of less than or equal to 16.

10. The method of claim 9, wherein said amphiphilic block copolymer has an HLB of less than or equal to 12.

11. The method of claim 10, wherein said amphiphilic block copolymer has an HLB of less than or equal to 8.

12. The method of claim 3, wherein the molecular weight of said poly(oxypropylene) segments of said amphiphilic block copolymer is greater than or equal to 1500 Da.

13. The method of claim 12, wherein said molecular weight is greater than or equal to 2000 Da.

14. The method of claim 13, wherein said molecular weight is greater than or equal to 2500 Da.

15. The method of claim 14, wherein said molecular weight is greater than or equal to 3000 Da.

16. The method of claim 2, wherein said protein is selected from the group consisting of cytokines; growth factors; amyloid beta binders; enkephalin; modulators of α-, β-, and/or γ-secretases; Glial-derived neutrotrophic factor (GDNF); vasoactive intestinal peptide; acid alpha-glucosidase (GAA); acid sphingomyelinase; iduronate-2-sultatase (I2S); α-L-iduronidase (IDU); β-Hexosaminidase A (HexA); Acid β-glucocerebrosidase; N-acetylgalactosamine-4-sulfatase; and α-galactosidase A.

17. The method of claim 16, wherein said protein is a growth factor selected from the group consisting of epidermal growth factor (EGF), basic fibroblast growth factor (bFGF), and nerve growth factor (NGF).

18. The method of claim 1, wherein said cleavable linker moiety linker is selected from the group consisting of:
—OC(O)NH(CH₂)₂NHC(O)(CH₂)₂SS(CH₂)₂C(O)NH—;
—OC(O)NH(CH₂)₂SS(CH₂)₂N═CH—; and
—OC(O)NH(CH₂)₂SS(CH₂)₂NH—.

19. A method for delivering a therapeutic agent across the blood-brain barrier into the central nervous system of an animal comprising administering to said animal a conjugate comprising said therapeutic agent conjugated to an amphiphilic block copolymer by a cleavable linker moiety, said cleavable linker moiety linker comprising a recognition site for a protease.

20. The method of claim 19, wherein said protease is selected from the group consisting of endosomal cathepsins, cathepsin B, lysosomal proteases, and colagenase.

21. The method of claim 19, wherein said recognition site for a protease is a sequence selected from the group consisting of GFLG (SEQ ID NO: 1); GLG (SEQ ID NO: 2); GGGLG-PAGGK (SEQ ID NO: 3); and KALGQPQ (SEQ ID NO: 4).

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: protease recognition site

<400> SEQUENCE: 1

Gly Phe Leu Gly
 1

<210> SEQ ID NO 2
<211> LENGTH: 3
<212> TYPE: PRT
<213> ORGANISM: Artificial Sequence
<220> FEATURE:
<223> OTHER INFORMATION: protease recognition site

<400> SEQUENCE: 2

Gly Leu Gly
 1

<210> SEQ ID NO 3
<211> LENGTH: 10
<212> TYPE: PRT
<213> ORGANISM: Artificial Sequence
<220> FEATURE:
<223> OTHER INFORMATION: protease recognition site

<400> SEQUENCE: 3

Gly Gly Gly Leu Gly Pro Ala Gly Gly Lys
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: protease recognition site

<400> SEQUENCE: 4

Lys Ala Leu Gly Gln Pro Gln
 1               5